United States Patent [19]
Dehdashtian et al.

[11] Patent Number: 6,110,191
[45] Date of Patent: Aug. 29, 2000

[54] ENDOVASCULAR DELIVERY SYSTEM

[75] Inventors: Mark Dehdashtian, Costa Mesa, Calif.; Weiyun Yu, Five Dock; Geoffrey H. White, East Balmain, both of Australia; Maria Lillian Saravia, Garden Grove, Calif.

[73] Assignee: Edwards Lifesciences, LLC, Irvine, Calif.

[21] Appl. No.: 09/203,998

[22] Filed: Dec. 1, 1998

Related U.S. Application Data

[63] Continuation of application No. 08/713,070, Sep. 12, 1996, Pat. No. 5,968,068.

[51] Int. Cl.[7] .................................................. A61M 29/00
[52] U.S. Cl. .............................. 606/192; 606/194; 604/96
[58] Field of Search ..................................... 606/192, 194, 606/108; 604/96

[56] References Cited

U.S. PATENT DOCUMENTS

| | | |
|---|---|---|
| 4,149,911 | 4/1979 | Clabburn . |
| 4,225,979 | 10/1980 | Rey et al. . |
| 4,306,318 | 12/1981 | Mano et al. . |
| 4,512,338 | 4/1985 | Balko et al. . |
| 4,553,545 | 11/1985 | Maass et al. . |
| 4,617,932 | 10/1986 | Kornberg . |
| 4,649,922 | 3/1987 | Wiktor . |
| 4,665,906 | 5/1987 | Jervis . |
| 4,665,918 | 5/1987 | Garza et al. . |

(List continued on next page.)

FOREIGN PATENT DOCUMENTS

| | | |
|---|---|---|
| 0177300 | 3/1986 | European Pat. Off. . |
| 0335341 | 10/1989 | European Pat. Off. . |
| 0421729 | 4/1991 | European Pat. Off. . |
| 0686379A2 | 12/1995 | European Pat. Off. . |
| 0792627A3 | 11/1997 | European Pat. Off. . |
| 2409747 | 10/1980 | France . |
| 2512678 | 11/1985 | France . |
| 2678508- A1 | 1/1993 | France . |
| 1766921 | 9/1970 | Germany . |
| 2189150 | 10/1987 | United Kingdom . |
| WO83/00997 | 3/1983 | WIPO . |
| WO90/04982 | 5/1990 | WIPO . |
| WO92/0004 | 1/1992 | WIPO . |
| WO95/08966 | 4/1995 | WIPO . |
| WO96/10375 | 4/1996 | WIPO . |
| WO96/28116 | 9/1996 | WIPO . |

Primary Examiner—Michael Buiz
Assistant Examiner—Julian W. Woo
Attorney, Agent, or Firm—Peter Jon Gluck; Edwards Lifesciences LLC; B. M. Canter

[57] ABSTRACT

A system for delivering and implanting a radially expandable endoluminal prosthesis within a body lumen (e.g., blood vessel). The system comprises a) an introducer/dilator assembly, and b) a delivery catheter/loader assembly. The introducer/dilator assembly comprises an elongate tubular introducer sheath which may be provided with a valving assembly mounted on the proximal end thereof. Such valving assembly may incorporate i) a hemostatic valve, ii) a first sealing valve and iii) a second sealing valve, positioned in series, to prevent leakage of body fluid out of the proximal end of the introducer and to permit two or more elongate members (e.g., catheters, guidewires) having differing outer diameters to be inserted through the introducer without leakage of body fluid therefrom. A dilator, which has regionalized differences in stiffness, is initially deployable within the lumen of the introducer to facilitate advancement of the introducer to its desired location within the body. Thereafter, the dilator may be removed from the introducer sheath and the delivery catheter/loader assembly may be attached to the introducer, such that the delivery catheter having the prosthesis mounted thereon may advanced through the introducer, to a desired location within the body. Thereafter, the radial expandable endoluminal prosthesis mounted on the delivery catheter is deployed and implanted by an expansion device (e.g., balloon) formed on the delivery catheter. The delivery catheter may incorporate one or more outflow apertures at specific location(s) to facilitate injection of radiographic contrast medium in a manner which will check for leakage around the endoluminal prosthesis, after the endoluminal prosthesis has been radially expanded and implanted.

2 Claims, 9 Drawing Sheets

U.S. PATENT DOCUMENTS

| | | |
|---|---|---|
| 4,681,110 | 7/1987 | Wiktor . |
| 4,728,328 | 5/1988 | Hughes et al. . |
| 4,729,766 | 5/1988 | Bergentz et al. . |
| 4,732,152 | 3/1988 | Wallsten et al. . |
| 4,762,128 | 8/1988 | Rosenbluth . |
| 4,772,264 | 9/1988 | Cragg . |
| 4,800,882 | 1/1989 | Gianturco . |
| 4,820,298 | 4/1989 | Leveen et al. . |
| 4,878,906 | 11/1989 | Lindemann et al. . |
| 4,886,062 | 12/1989 | Wiktor . |
| 4,886,065 | 12/1989 | Collins, Jr. . |
| 4,913,141 | 4/1990 | Hillstead . |
| 4,969,458 | 11/1990 | Wiktor . |
| 4,969,890 | 11/1990 | Sugita et al. . |
| 4,994,071 | 2/1991 | MacGregor . |
| 5,019,090 | 5/1991 | Pinchuk . |
| 5,037,427 | 9/1991 | Harada et al. . |
| 5,047,050 | 9/1991 | Arpesani . |
| 5,057,092 | 10/1991 | Webster, Jr. . |
| 5,064,435 | 11/1991 | Porter . |
| 5,067,957 | 11/1991 | Jervis . |
| 5,078,726 | 1/1991 | Kreamer . |
| 5,078,736 | 1/1991 | Behl . |
| 5,085,635 | 2/1992 | Cragg . |
| 5,104,404 | 4/1992 | Wolff . |
| 5,133,732 | 7/1992 | Wiktor . |
| 5,183,085 | 2/1993 | Timmermans . |
| 5,192,297 | 3/1993 | Hull . |
| 5,201,901 | 4/1993 | Harada et al. . |
| 5,207,695 | 5/1993 | Trout, III . |
| 5,236,446 | 8/1993 | Dumon . |
| 5,275,622 | 1/1994 | Lazarus et al. . |
| 5,342,387 | 8/1994 | Summers . |
| 5,354,309 | 10/1994 | Schnepp-Pesch et al. . |
| 5,366,504 | 11/1994 | Andersen et al. . |
| 5,383,928 | 1/1995 | Scott et al. . |
| 5,387,235 | 2/1995 | Chuter . |
| 5,397,345 | 3/1995 | Lazarus . |
| 5,415,664 | 5/1995 | Pinchuk . |
| 5,429,144 | 7/1995 | Wilk . |
| 5,443,496 | 8/1995 | Schwartz et al. . |
| 5,443,498 | 8/1995 | Fontaine . |
| 5,456,713 | 10/1995 | Chuter . |
| 5,464,449 | 11/1995 | Ryan et al. . |
| 5,507,767 | 4/1996 | Maeda et al. . |
| 5,507,771 | 4/1996 | Gianturco . |
| 5,562,724 | 10/1996 | Vorwerk et al. . |
| 5,562,727 | 10/1996 | Turk et al. . |
| 5,562,728 | 10/1996 | Lazarus et al. . |
| 5,571,170 | 11/1996 | Palmaz et al. . |
| 5,575,817 | 11/1996 | Martin . |
| 5,609,627 | 3/1997 | Goicoechea et al. ............ 606/194 |
| 5,683,450 | 11/1997 | Goicoechea et al. . |
| 5,683,451 | 11/1997 | Lenker et al. . |
| 5,693,086 | 12/1997 | Goicoechea et al. . |
| 5,709,713 | 1/1998 | Evans et al. . |
| 5,716,365 | 2/1998 | Goicoechea et al. . |
| 5,718,724 | 2/1998 | Goicoechea et al. . |
| 5,752,522 | 5/1998 | Murphy . |
| 5,782,904 | 7/1998 | White et al. . |
| 5,860,923 | 1/1999 | Lenker et al. . |

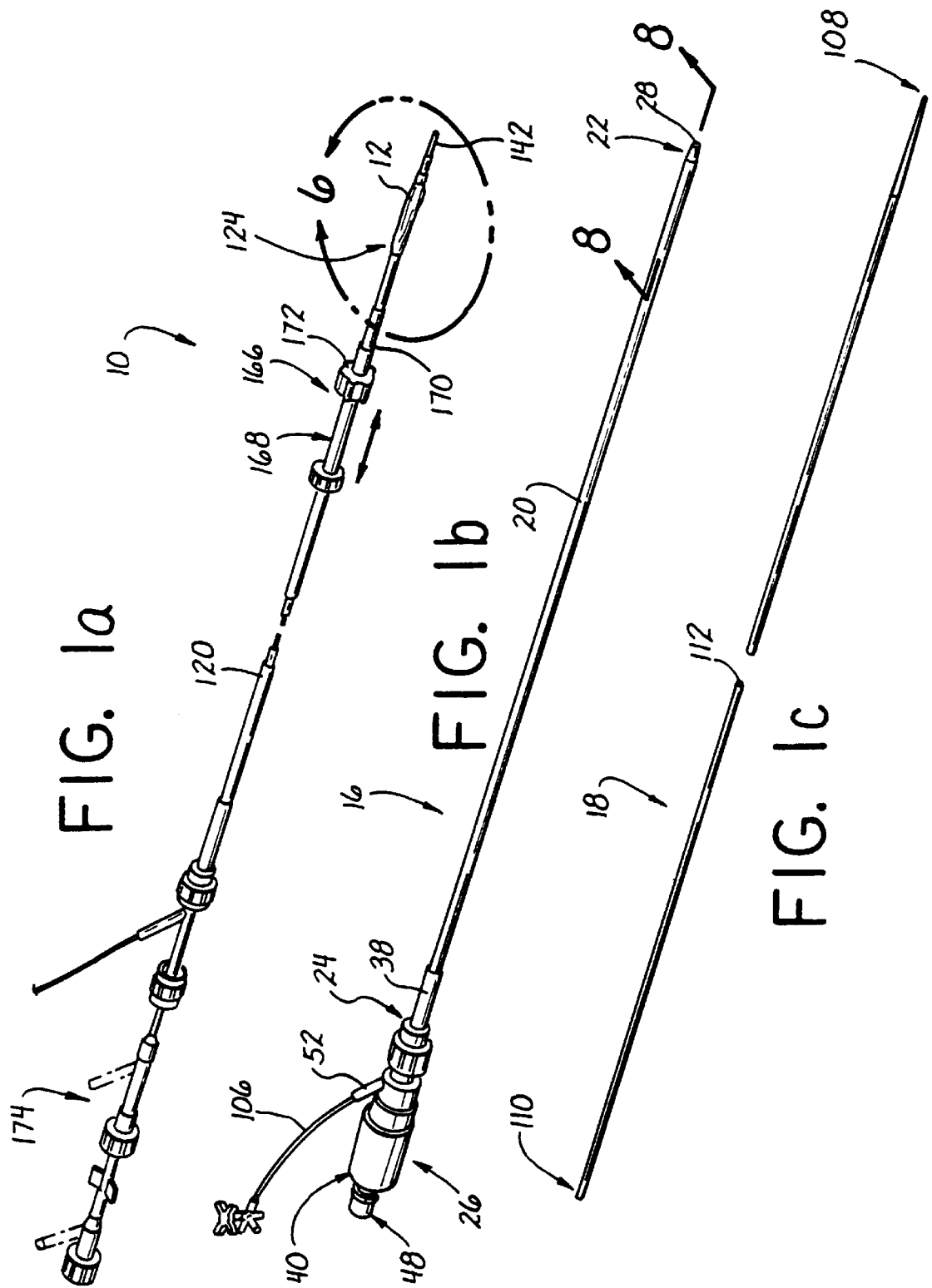

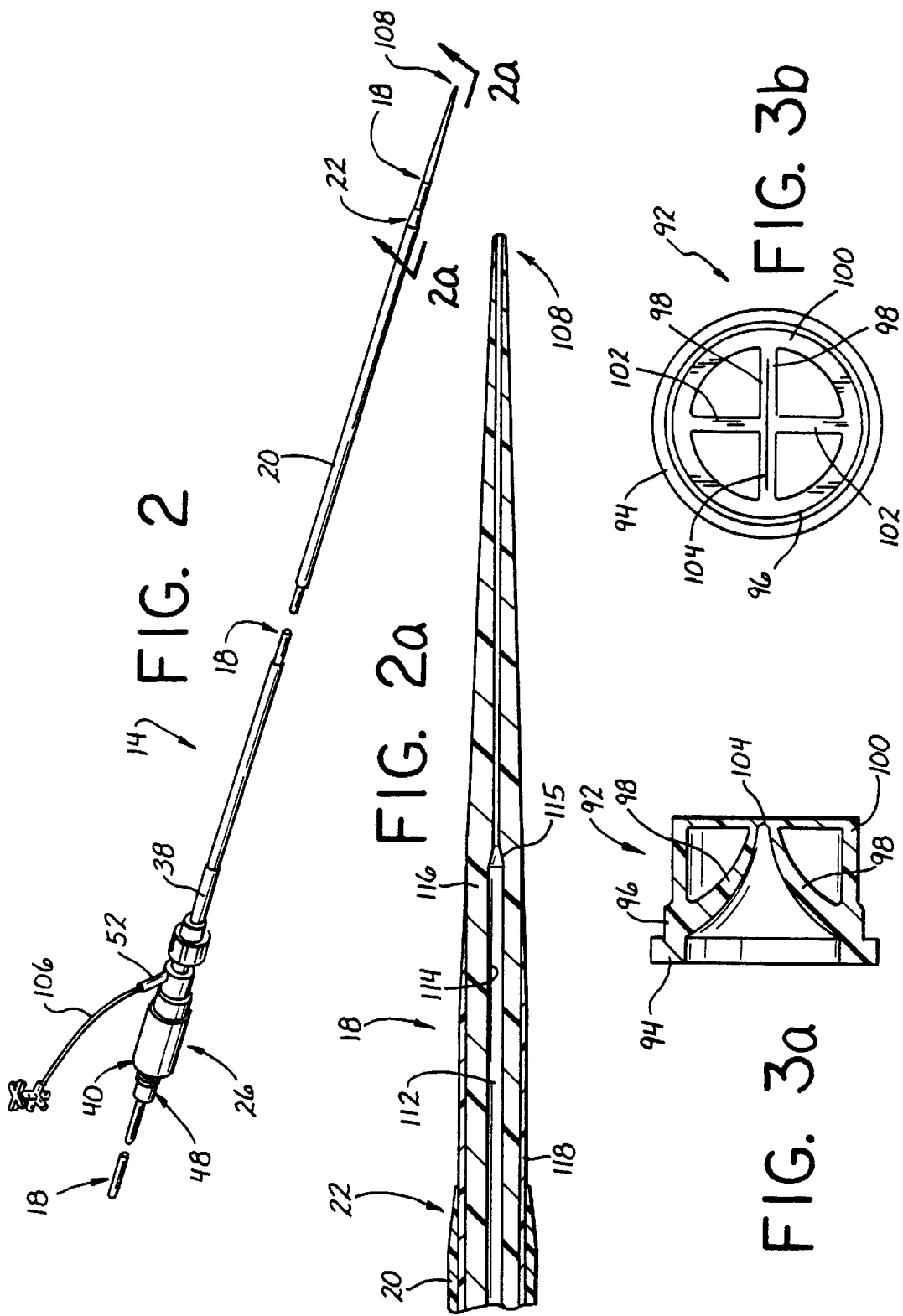

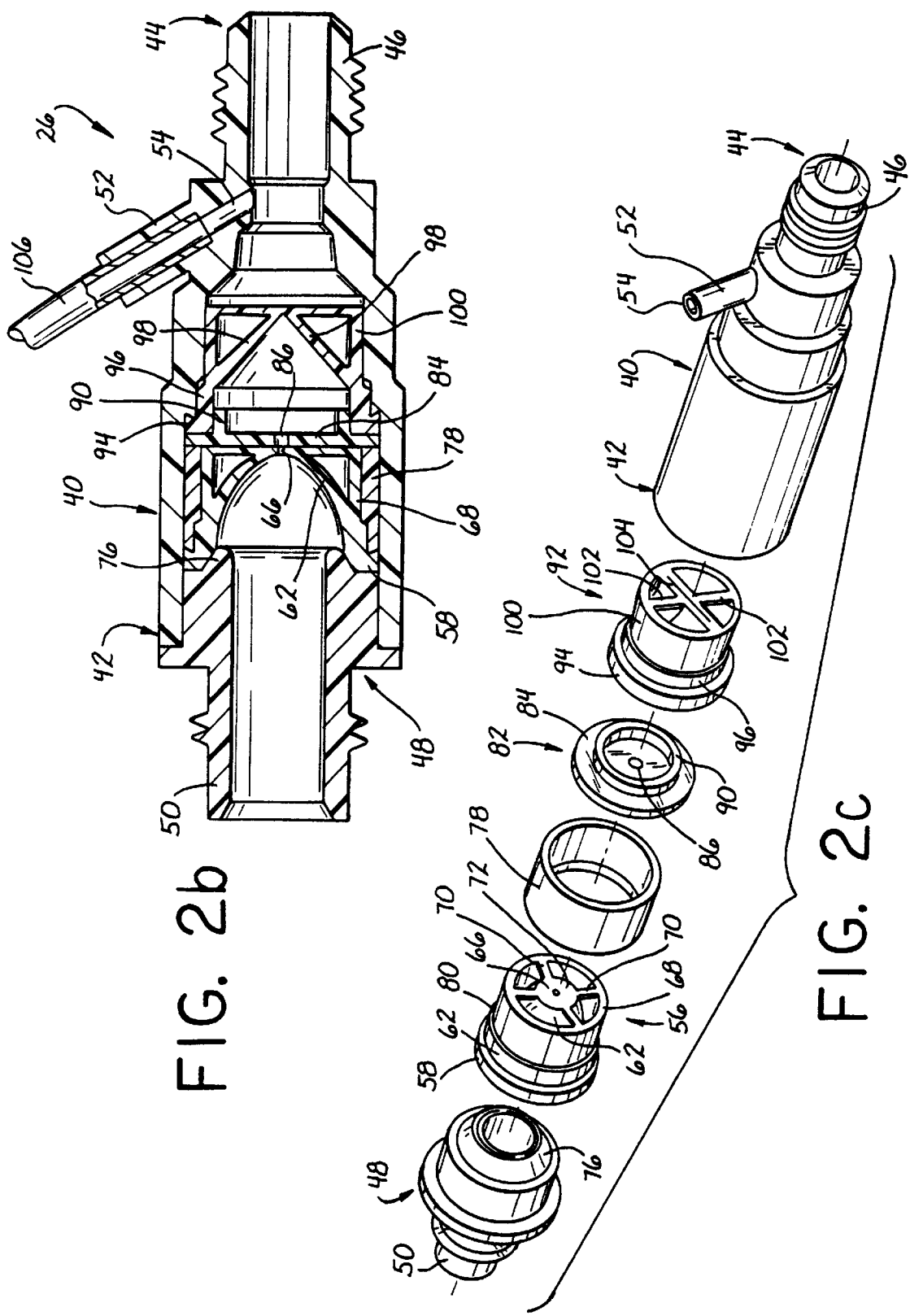

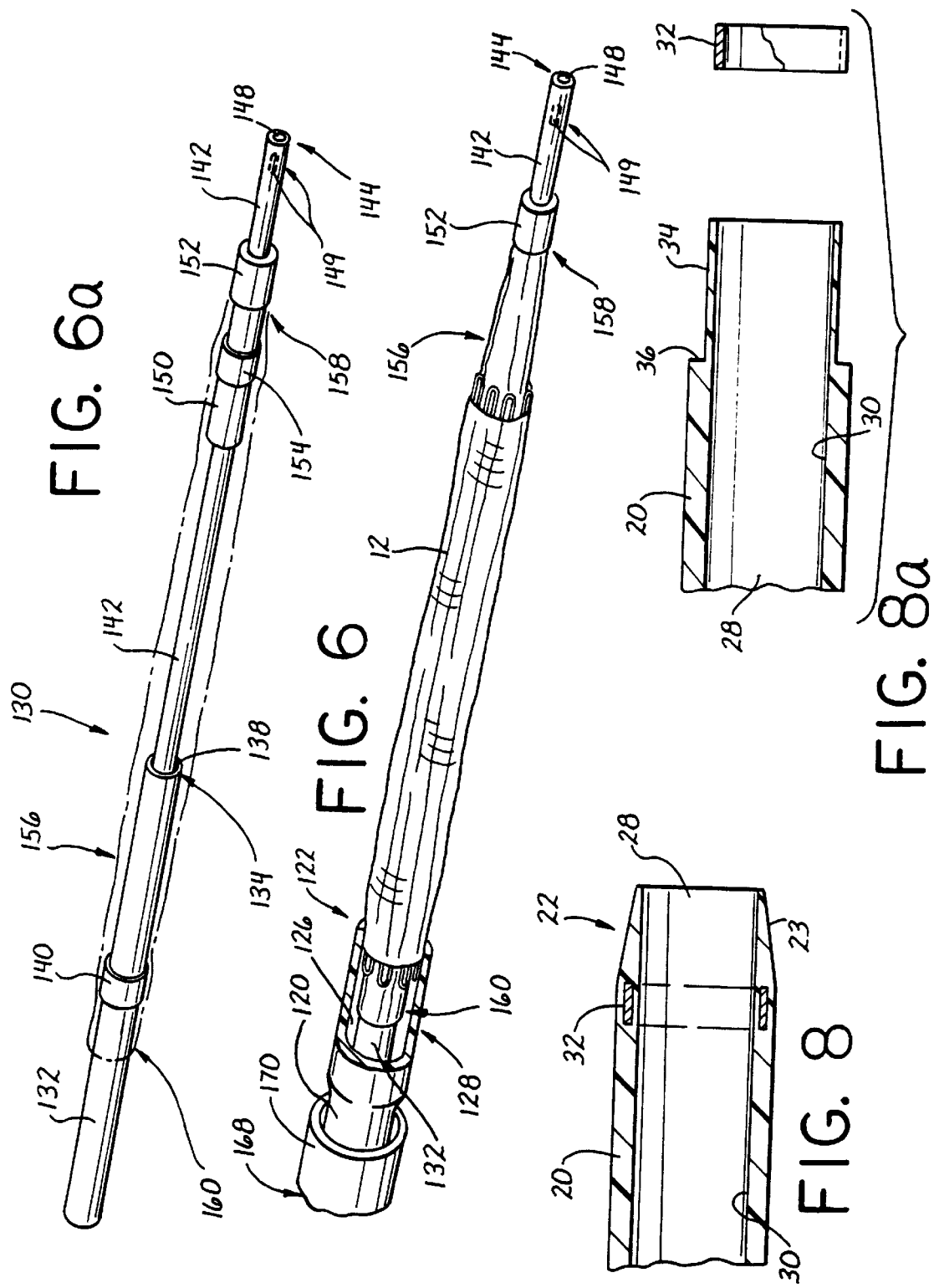

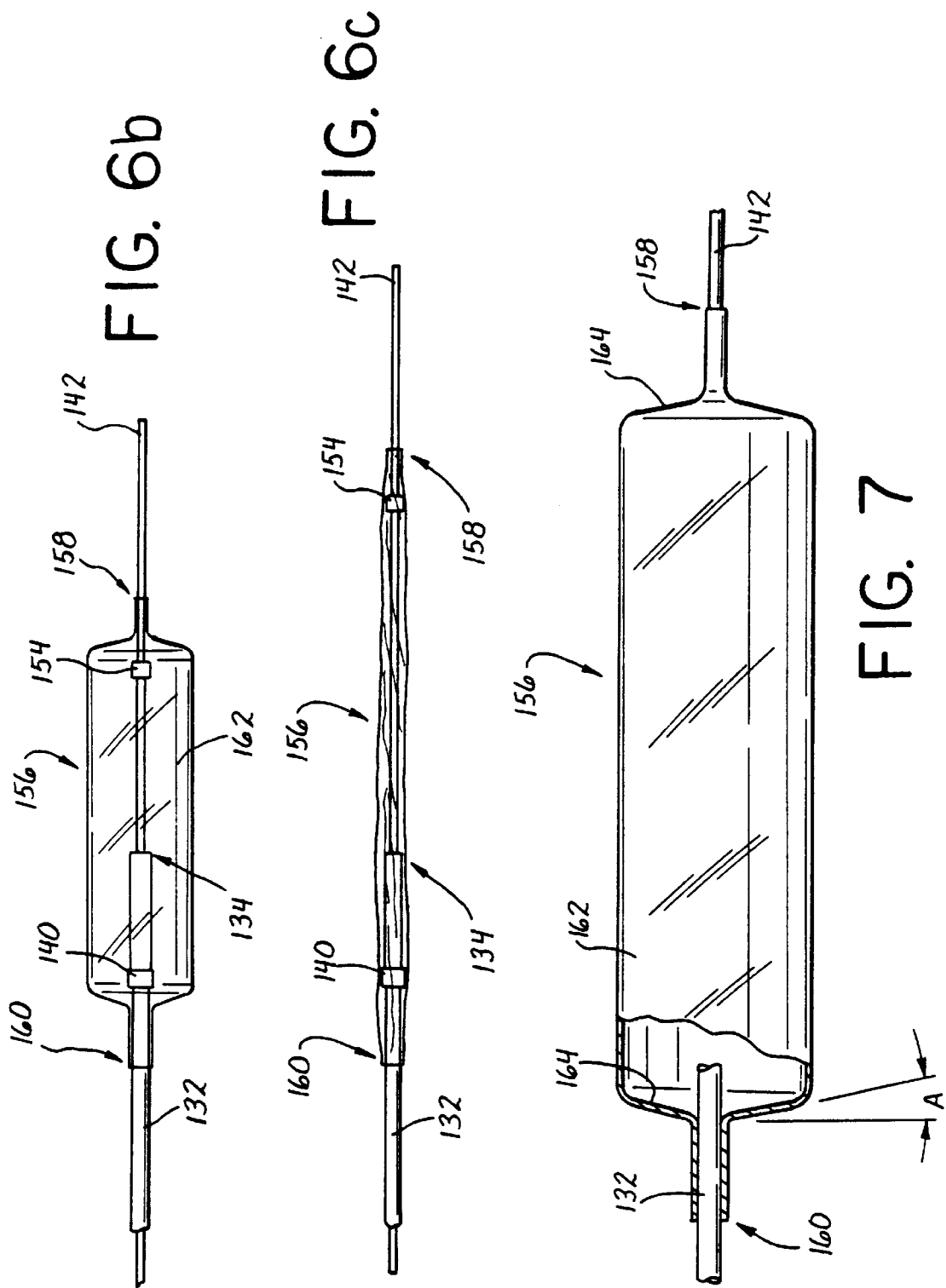

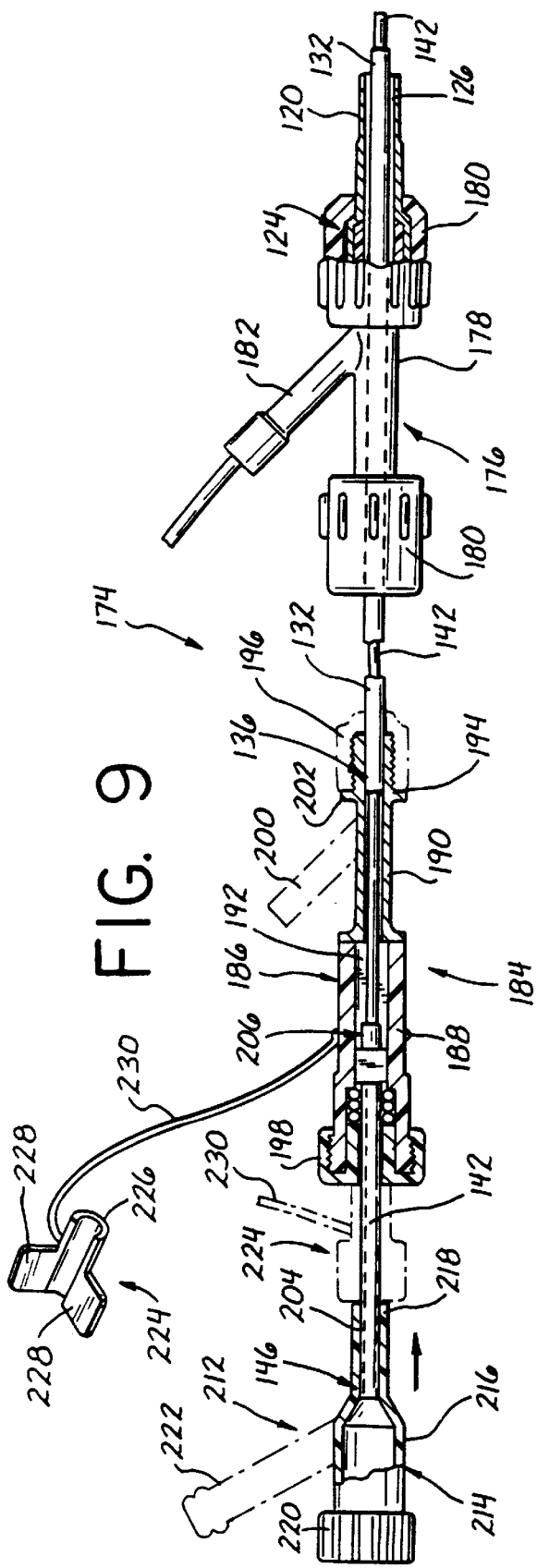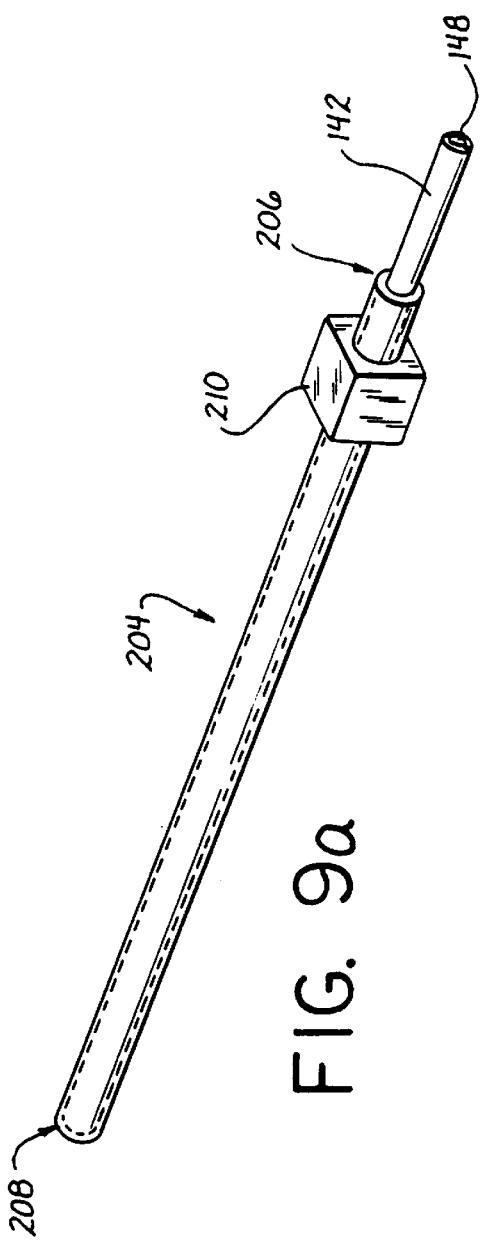

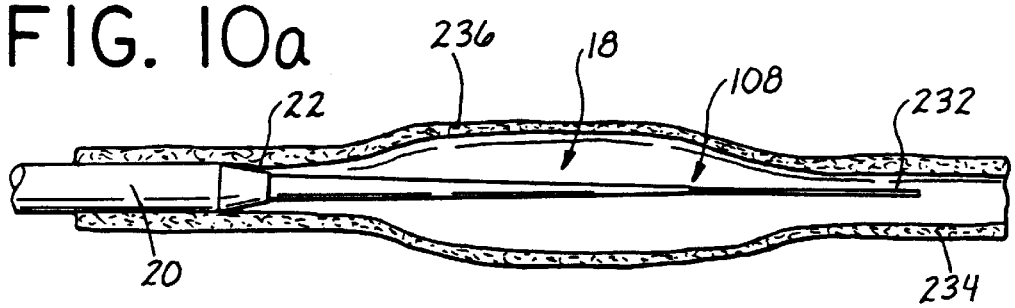
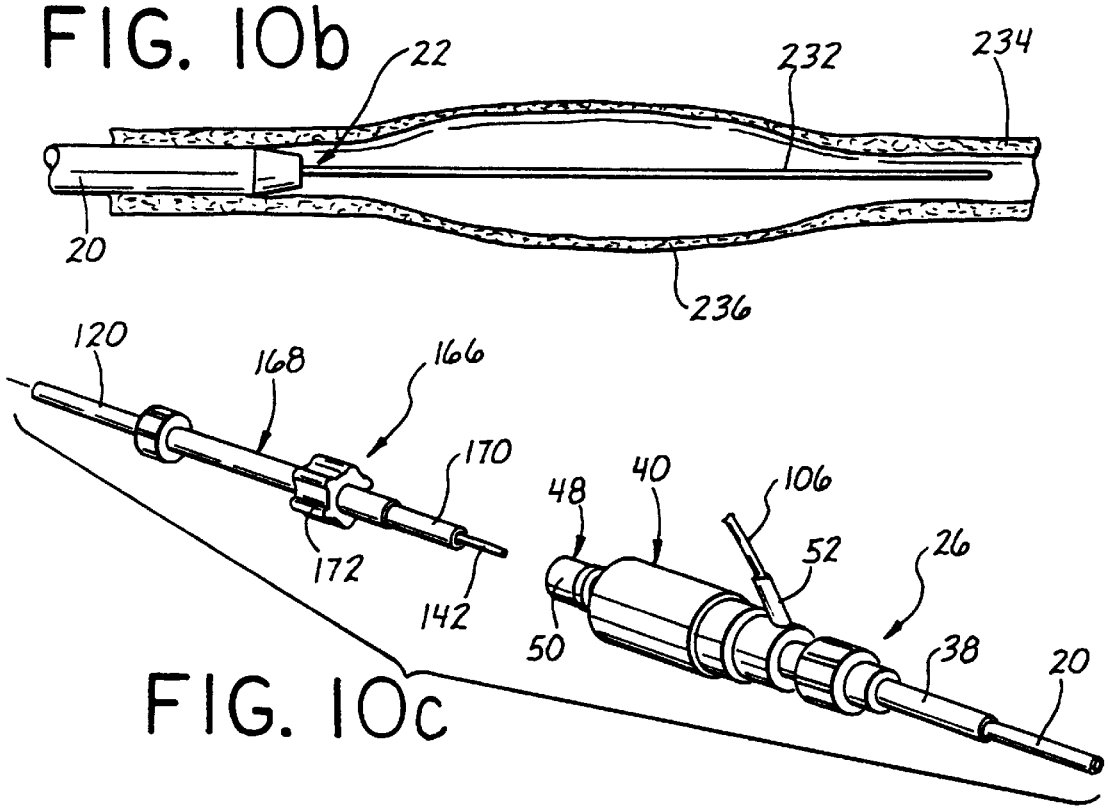
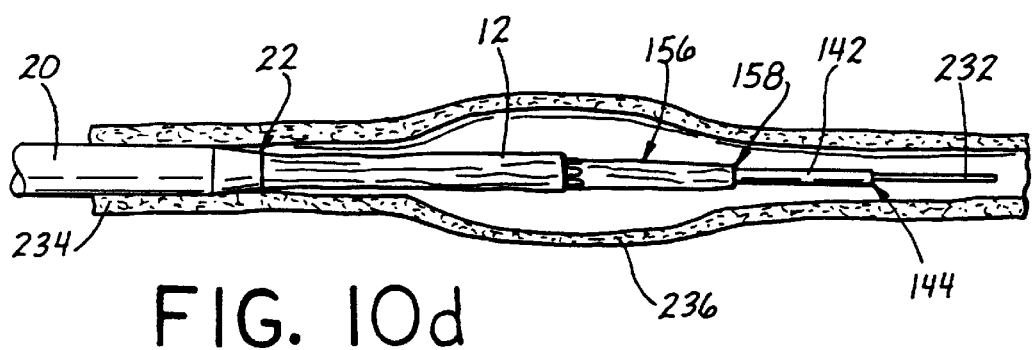

ENDOVASCULAR DELIVERY SYSTEM

This is a continuation, of application Ser. No. 08/713,070, filed Sep.12, 1996, now U.S. Pat. No. 5,968,068.

FIELD OF THE INVENTION

The present invention pertains generally to medical devices, and more particularly to a catheter delivery system for endovascular stents and endovascular grafts.

BACKGROUND OF THE INVENTION

The term "stent" is generally used to describe endoprosthetic devices which are implanted in blood vessels or other anatomical passageways of the body for the purpose of treating stenoses, aneurysms, occlusions, etc. Typically, such stents are implanted in blood vessels to maintain dilation and patency of an occluded region of blood vessel, or to bridge a weakened or aneurysmic region of blood vessel. On the other hand, some typical non-vascular applications of such stents are for the treatment of constrictions or injuries to the gastrointestinal tract (e.g., esophagus), ducts of the biliary tree (e.g., common bile duct) or anatomical passageways of the genitourinary tract (e.g., ureter, urethra fallopian tube, etc.).

Most stents are initially disposed in a compact configuration of relatively small diameter, whereby the stent may be mounted upon or within a delivery catheter for insertion and transluminal advancement into the desired anatomical passageway. Thereafter, such stents are radially expandable to a larger "operative" diameter which is equal to or slightly larger than the diameter of the blood vessel or other anatomical passageway in which the stent is to be implanted. When radially expanded to such operative diameter, the stent will typically become released from the delivery catheter and embedded or engaged to the surrounding wall of the blood vessel or other anatomical passageway.

Some stents are covered with tubular sleeves, in which case they are typically referred to as a "stented graft".

In general, stents and stented grafts fall into two major categories—a) self-expanding and b) pressure-expandable. Those of the self-expanding variety may be formed of resilient or shape memory material (e.g., spring steel or nitinol™) which is capable of self-expanding from its first (radially compact) diameter to its second (operative) diameter without the exertion of outwardly-directed force against the stent or stented graft. Examples of such self-expanding stents and stented grafts are set forth in U.S. Pat. Nos. 4,655,771 (Wallsten, et al); 4,954,126 (Wallsten); 5,061,275 (Wallsten, et al); 4,580,568 (Gianturco); 4,830,003 (Wolf, et al); 5,035,706 (Gianturco, et al); 5,330,400 (Song) and 5,354,308 (Simon, et al) and Foreign Patent Publication Nos. WO94\12136; WO92\06734 and EPA183372. Those of the pressure-expandable (i.e., "passive expandable") variety may be formed of plastically deformable material (e.g., stainless steel) which is initially formed in its first (radially compact) diameter and remains stable in such first diameter until such time of outwardly directed pressure is exerted upon the stent or stented graft to cause radial expansion and resultant plastic deformation of the stent or stented graft, to its second (operative) diameter. Examples of such pressure-expandable stents and stented grafts are set forth in U.S. Pat. Nos. 5,135,536 (Hillstead); 5,161,547 (Tower); 5,292,331 (Boneau); 5,304,200 (Spaulding); 4,733,665 (Palmaz); 5,282,823 (Schwartz, et al); 4,776,337 (Palmaz); and 5,403,341 (Solar) and Foreign Patent Publication Nos. EPA480667; and WO95\08966.

In many applications, careful positioning and firm implantation of the stent or stented graft is critical to the successful treatment of the underlying medical problem. In this regard, the delivery catheter which is utilized to accomplish the positioning and implantation of the stent or stented graft is an important aspect of the overall system. Various types of delivery catheters for stents and stented grafts have been previously known, including those described in U.S. Pat. Nos. 4,665,918 (Garza, et al); 4,733,665 (Palmaz); 4,739,762 (Palmaz); 4,762,125 (Leiman, et al);,776,337 (Palmaz); 4,838,269 (Robinson, et al); 4,994,071 (MacGregor); 5,037,427 (Harada, et al); 5,089,005 (Harada); 5,102,417 (Palmaz); 5,108,416 (Ryan, et al); 5,141,498 (Christian); 5,181,920 (Mueller, et al); 5,195,984 (Schatz); 5,201,901 (Harada, et al); 5,269,763 (Boehmer, et al); 5,275,622 (Lazarus, et al); 5,290,295 (Querals, et al); 5,306,294 (Winston, et al); 5,318,588 (Horzewski, et al); 5,344,426 (Lau, et al); 5,350,363 (Goode, et al); 5,360,401 (Turnland); 5,391,172 (Williams, et al); 5,397,345 (Lazarus); 5,405,380 (Gianotti, et al); 5,443,452 (Hart, et al); 5,453,090 (Martinez, et al); 5,456,284 (Ryan, et al); and 5,456,694 (Marin, et al) and Foreign Patent Publication Nos. EP-0308-815-A2; EP-0335-341-A1; EP-364-787-A; EP-0442-657-A2; EP-482976-A; EP-0505-686-A1; EP-0611-556-A1; EP-0638-290-A1; WO94\15549; WO95\01761; GB2196-857-A; DE3042-229; and DE3737-121-A. Generally, the attributes which are desirable of any delivery catheter which is to be used for placement and implantation of stents or stented grafts, are as follows:

a) maintain minimal diameter during insertion to avoid unnecessary trauma and/or difficulty of placement;

b) include radiopaque markings at appropriate locations to facilitate precise visualization and positioning of the delivery catheter to ensure that the stent or stented graft is implanted at the desired location;

c) reliable and reproducible expansion of the stent or stented graft to its full operative diameter, without regional or localized variations in the degree or completeness of such expansion;

d) reliable and reproducible disengagement or release of the stent or stented graft from the catheter body;

e) ability to withdraw and remove the delivery catheter without disturbing the newly implanted stent or stented graft; and, f) ability to easily check for leakage of biological fluid (e.g., blood) outside of a stented graft (i.e., an "endoleak") after the stented graft has been delivered and implanted within a body lumen.

None of the previously-known delivery catheter systems have been clearly optimal for all types of stents and stented grafts. Accordingly, there remains a need in the art for a design and development of improved delivery catheter systems for at least some types of stents and stented grafts.

SUMMARY OF THE INVENTION

The present invention provides a method and system for implanting a tubular endoluminal prosthesis (e.g., a stent or stented graft) within a body lumen (e.g., artery, vein, gastrointestinal tract, ducts of the biliary tree, urinary tract, reproductive tract, or other endocrine or exocrine ducts, etc.) of a mammal. The system of the present invention includes a) a delivery catheter; b) an introducer assembly; and c) a dilator.

In accordance with the invention, there is provided a delivery catheter which is usable for introducing and implanting a radially expandable tubular endoluminal prosthesis within a duct of the body. The delivery catheter incorporates one or more of the following elements:

a) a portion of the catheter being formed of separate tubular members upon which opposite ends of a radially expandable balloon are mounted such that movement (e.g., longitudinal, rotational) movement of one of such members relative to the other will cause the balloon to be tightened (e.g., longitudinally drawn, rotatably twisted) to a taut configuration when the balloon is in its deflated state, thereby eliminating or minimizing loose or protrusive balloon material which may interfere with subsequent retraction and removal of the delivery catheter; and/or, b) a non-tapered or minimally-tapered balloon which is usable to radially expand the tubular intraluminal prosthesis, said balloon being mounted on the body of the delivery catheter and comprising:
   i) a substantially cylindrical sidewall which is disposed coaxially about the longitudinal axis of the delivery catheter,
   ii) a proximal end wall which extends from the proximal end of the cylindrical sidewall to the outer surface of the catheter body; and
   iii) a distal end wall which extends from the distal end of the cylindrical sidewall to the outer surface of the catheter body, said proximal and distal end walls being disposed at angles which are no more than ten (10) degrees from perpendicular to the longitudinal axis of the catheter body; and/or, c) a loader assembly for facilitating introduction of the distal portion of the catheter and a radially-compact intraluminal prosthesis mounted thereon, into a tubular introducer. Such loader assembly may comprise a tubular sheath which is advancable over the radially compact intraluminal prosthesis mounted on the catheter body, and which is directly engageable to the proximal end of an introducer so as to facilitate subsequent advancement in introduction of the radially compact intraluminal prosthesis into the lumen of the introducer; and/or, d) one or more radiographic contrast medium outflow apertures in communication with a radiographic contrast medium infusion lumen extending longitudinally through the catheter, said outflow aperture(s) being positioned on the catheter at a location whereby radiographic contrast medium may be infused through the lumen and out of the outflow aperture(s) into the body lumen wherein the endoluminal prosthesis has been implanted, at a location upstream of the endoluminal prosthesis, such that said radiographic contrast medium will migrate outside of the endoluminal prosthesis if endoleak(s) exist whereby endogenous fluid flowing through the body lumen is seeping or leaking around the endoluminal prosthesis due to inadequate or imperfect implantation and abutment of the endoluminal prosthesis against the body lumen in which it is implanted.

Further in accordance with the invention, there is provided an introducer assembly comprising an elongate tubular introducer sheath having one or more of the following elements:

a) an embedded radiopaque marker which comprises a ring or segment of radiopaque material which has been melted or otherwise embedded within the wall of the introducer sheath so as to be fully surrounded or encapsulated by the material of the introducer sheath, while remaining visible by radiographic means; and/or, b) a valving assembly (e.g., "valving head") mounted on the introducer sheath in alignment with the lumen of the introducer sheath, said valving assembly comprising:
   i) a hemostatic valve (e.g., a "duck bull" check valve) positioned in longitudinal alignment with said introducer lumen, said hemostatic valve comprising a pliable hemostatic valve body having a self-sealing passageway formed therein, said self-sealing passageway being biased to a closed configuration whereby blood is substantially blocked from backflowing in the proximal direction through said hemostatic valve when no elongate member is inserted through the introducer lumen, said self-sealing passageway being enlargeable to permit first and second elongate members of said first and second outer diameters to pass therethrough;
   ii) a first sealing valve (e.g., an elastomeric valve having a cross-slit opening formed therein) in longitudinal alignment with said hemostatic valve, said first sealing valve comprising a pliable first sealing valve body having a first sealing valve opening formed therein, said first sealing valve opening being initially of a first diameter which will allow said first elongate member to pass therethrough, and enlargeable to a second diameter which will allow said second elongate member to pass therethrough in sealing contact with said first sealing valve body such that blood will be prevented from backflowing in the proximal direction through said first sealing valve while said second elongate member is inserted therethrough; and,
   iii) a second sealing valve (e.g., an elastomeric disc. valve having an annular opening formed therein) in longitudinal alignment with said first sealing valve and said hemostatic valve, said second sealing valve comprising a pliable second sealing valve body having a second sealing valve opening formed therein, said second sealing valve opening being initially of a first diameter which will allow said first elongate member to pass therethrough in sealing contact with said second sealing valve body such that blood will be prevented from backflowing in the proximal direction through said second sealing valve when said first elongate member is inserted therethrough, and being enlargeable to at least said second diameter to allow said second elongate member to pass therethrough.

In embodiments wherein the introducer sheath incorporates the valving assembly mounted on the introducer sheath, such valving assembly may be positioned on the proximal end of the introducer sheath and may be volitionally detachable therefrom so as to permit interchangeability of the introducer sheath without requiring the use of multiple valving assemblies. Also, the proximal end of the introducer sheath (or of the valving assembly if positioned thereon) may be provided with threads or other engagement members to permit a loader assembly to be positively engaged (e.g., locked) thereto, thereby facilitating smooth advancement of a delivery catheter having an endoluminal prosthesis mounted thereon into and through the lumen of the introducer sheath.

Still further in accordance with the invention, there is provided a dilator which is insertable through the lumen of an introducer sheath to dilate an intersticial puncture tract to the diameter of the introducer sheath, said dilator comprising an outer tube formed of a first material and an inner cylindrical member formed of a second material which is softer than the first material. A distal portion of the outer tubular member is removed and the adjacent material of the inner cylindrical member is tapered by way of a radio frequency process or machining process, thereby exposing a tapered segment of the relatively soft inner cylindrical member at the distal end of the dilator, while allowing the proximal portion of the dilator to remain sheathed by the relatively hard outer tubular member. A guidewire lumen may extend longitudinally through the inner cylindrical member to permit the dilator to be advanced over a pre-inserted guidewire.

When constructed in this manner, the distal end of the dilator is sufficiently soft to be advanced through tortuous anatomical structure such as blood vessels without causing undue trauma or perforation thereof, while the proximal portion of the dilator is sufficiently rigid to perform an anatomy-straightening function whereby pliable anatomical structures (e.g., blood vessels) wherein the dilator is advanced will be urged or brought toward linear alignment with one another by virtue of advancement of the relatively rigid proximal portion of the dilator therethrough. In this manner, the dilator may facilitate ease of advancement of the distal end of the introducer to a desired location (e.g, within the distal portion of the abdominal aorta) even though it must pass through relatively tortuous anatomical passageways (e.g., the femoral and iliac arteries).

In accordance of the methodology of the present invention, the above-described dilator is initially insertable through the lumen of the introducer sheath such that the pliable, tapered distal portion of the dilator protrudes out of and beyond the distal end of the introducer sheath. Thereafter, the introducer sheath/dilator combination is insertable through an intersticial tract into a blood vessel or other body lumen such that the relatively soft distal portion of the dilator and the distal end of the introducer are located within the body lumen. Thereafter, the dilator is extracted and removed from the introducer sheath, and the valving assembly of the introducer sheath (if present) will prevent backflow or leakage of blood or other body fluid out of the proximal end of the introducer sheath. Thereafter, the loader assembly of the delivery catheter (if present) is engageable with the proximal end of the introducer sheath and the delivery catheter, having the radially expandable endoluminal prosthesis mounted thereon, is advanced through the introducer sheath until the balloon and accompanying endoluminal prosthesis are located at the desired implantation site within the body lumen. Thereafter, the balloon is inflated to cause radial expansion and implantation of the endoluminal prosthesis. Thereafter, the balloon is deflated and the catheter assembly is longitudinally telescoped or elongated (if such capability exists) to draw the deflated balloon to a taut configuration such that the delivery catheter and deflated balloon may be extracted and removed without fouling or snagging the radially expanded and implanted endoluminal prosthesis.

Further objects and advantages of the present invention will become apparent to those skilled in the art upon reading and understanding of the following detailed description and accompanying drawings.

BRIEF DESCRIPTION OF THE DRAWINGS

These, as well as other features of the present invention, will become more apparent upon reference to the drawings wherein:

FIG. 1a is a front perspective view of the catheter assembly of the delivery system constructed in accordance with the present invention;

FIG. 1b is a front perspective view of the sheath assembly of the introducer assembly shown in FIG. 2;

FIG. 1c is a front perspective view of the dilator of the introducer assembly shown in FIG. 2;

FIG. 2 is a front perspective view of the introducer assembly of the delivery system constructed in accordance with the present invention;

FIG. 2a is a cross-sectional view of the distal portion of the introducer assembly taken along line 2a—2a of FIG. 2;

FIG. 2b is a cross-sectional view of the valve head of the sheath assembly shown in FIG. 1b;

FIG. 2c is an exploded view of the valve head shown in FIG. 2b;

FIG. 3a is a cross-sectional view of the hemostatic valve included in the valve head shown in FIGS. 2b and 2c;

FIG. 3b is a side elevational view of the hemostatic valve shown in FIG. 3a;

FIG. 4b is a side elevational view of the disc valve shown in FIG. 4a;

FIG. 5b is a side elevational view of the cross slit valve shown in FIG. 5a;

FIG. 6 is an enlarged perspective view of the encircled region 6 shown in FIG. 1a, illustrating the balloon and graft of the catheter assembly in collapsed orientations;

FIG. 6a is a front perspective view of the proximal portion of the catheter assembly illustrating the manner in which the balloon is attached thereto;

FIG. 6b is a side elevational view of the catheter assembly as oriented in a first, retracted position when the balloon thereof is inflated;

FIG. 6c is a side elevational view of the catheter assembly as oriented in a second, extended position subsequent to the deflation of the balloon thereof;

FIG. 7 is a partial cross-sectional view of the balloon of the catheter assembly;

FIG. 8 is a cross-sectional view taken along line 8—8 of FIG. 1b, illustrating the marker embedded in the distal portion of the sheath assembly;

FIG. 8a is an exploded view illustrating the manner in which the marker shown in FIG. 8 is embedded in the distal portion of the sheath assembly;

FIG. 9 is a partial cross-sectional view of the catheter assembly shown in FIG. 1a, illustrating the components included in the distal portion thereof;

FIG. 9a is a front perspective view illustrating the manner in which an anti-rotation member is integrated into the proximal portion of the catheter assembly shown in FIG. 9; and FIGS. 10a–10h are cross-sectional views illustrating the sequence of steps practiced in an exemplary procedure utilizing the endovascular delivery system of the present invention.

DETAILED DESCRIPTION OF THE PREFERRED EMBODIMENT

Figure 4A:
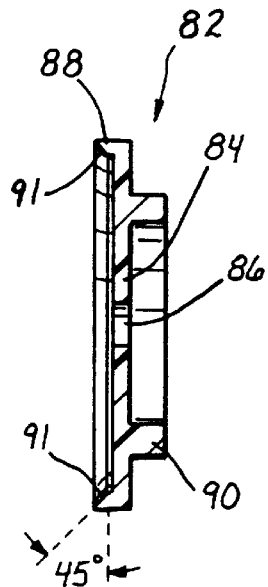
FIG. 4a is a cross-sectional view of the disc valve included in the valve head shown in FIGS. 2b and 2c.

Referring now to the drawings wherein the showings are for purposes of illustrating a preferred embodiment of the present invention only, and not for purposes of limiting the same, FIG. 1a perspectively illustrates the catheter assembly 10 of the endovascular delivery system of the present invention. In accordance with the present invention, the delivery system is used to facilitate the placement of an intraluminal graft 12 into a desired anatomical passageway. The graft 12 with which the catheter assembly 10 is preferably utilized is fully disclosed in PCT Patent Application No. WO 95/08966 entitled INTRALUMINAL GRAFT and Australian Provisional Specification No. PN-6513 entitled POSITIONING AN INTRALUMINAL GRAFT USING A GUIDEWIRE AND A CATHETER THEREFORE filed Nov. 10, 1995. As will be discussed in more detail below, the endovascular delivery system of the present invention finds particular utility in relation to the use of a tubular endovascular graft 12 for the bridging (i.e., creating a tubular passageway through) an aortic aneurysm. However, those of ordinary skill in the art will recognize that the present invention will be useable for many other medical applications as well, and may be used to facilitate the operative placement of various types of intraluminal devices (e.g., stents, stented grafts, etc.) in many types of vascular and non-vascular body lumens (e.g., veins, arteries, esophagus, ducts of the biliary tree, intestine, ureter, urethra, fallopian tube, other endocrine or exocrine ducts, etc.).

Referring now to FIG. 2, in addition to the catheter assembly 10 upon which the graft 12 is initially positioned, the endovascular delivery system of the present invention further comprises an introducer assembly 14. The introducer assembly 14 is used to facilitate the advancement of the catheter assembly 10, and more particularly the graft 12 positioned thereupon, to a desired intraluminal site. In applications of the invention wherein an endovascular graft is being implanted in the abdominal aorta to bridge or recannalize an aortic aneurysm, the introducer assembly 14 is used to facilitate the introduction of the catheter assembly 10 into a femoral artery and into a site in the aorta located between the left and right iliac arteries and the renal arteries. It is in this particular aortic site where occurrences of aortic aneurysms are most common. The introducer assembly 14 itself comprises two (2) primary components, i.e., a sheath assembly 16 (shown in FIG. 1b) and an elongate dilator 18 (shown in FIG. 1c) which initially resides within the sheath assembly 16. The structural attributes of the catheter assembly 10 and introducer assembly 14 (including the sheath assembly 16 and dilator 18) will be separately described in detail in the following paragraphs. The detailed description of the various components comprising the endovascular delivery system of the present invention will be followed by a discussion regarding a preferred manner of using the same in relation to the treatment of aortic aneurysms.

A. Introducer Assembly

As previously indicated, the operative placement of the catheter assembly 10, and more particularly the graft 12 positioned thereupon, in a desired intraluminal site is facilitated through the use of the introducer assembly 14 shown in FIG. 2. As also previously indicated, the introducer assembly 14 itself comprises a sheath assembly 16 and a dilator 18, the precise structures of which will now be described with particular reference to FIGS. 1b 5b, 8 and 8a.

1. Sheath Assembly

The introducer assembly 14 of the present invention comprises a sheath assembly 16 which includes an elongate, tubular sheath 20 having a tapered distal end 22 and a proximal end 24. Coupled to the proximal end 24 of the sheath 20 is a valve head 26 which is shown in cross-section in FIG. 2b.

Referring now to FIGS. 1b, 8 and 8a, the sheath 20 of the sheath assembly 16 is preferably fabricated from polypropylene, and includes a lumen 28 extending longitudinally therethrough which is defined by a smooth, intraluminal surface 30. As previously indicated, the distal end 22 of the sheath 20 is preferably formed to have an annular tapered surface 23. Additionally, as best seen in FIG. 8, embedded within the sheath 20 adjacent the tapered distal end 22 thereof is an annular, radiopaque marker 32. The preferred composition of the marker 32 is 90% platinum, 10% iridium.

With reference to FIG. 8a, the embedding of the marker 32 within the sheath 20 is facilitated by initially removing material from the distal portion of the sheath 20 such that the same defines a distal section 34 having an outer diameter which is substantially less than that of the remainder of the sheath 20, and is separated thereby by a stepped annular shoulder 36. Subsequent to the formation of the reduced diameter distal section 34, the annular marker 32 is slidably advanced thereover into abutting contact with the shoulder 36. The marker 32 is sized such that the inner surface thereof rests directly upon the outer surface of the distal section 34, with the outer surface of the marker 32 being disposed radially inward relative to the outer surface of the remainder of the sheath 20. Subsequent to the advancement of the marker 32 over the distal section 34 in the aforementioned manner, the distal portion of the sheath 20 is inserted into a suitable fixture and subjected to an RF heating process which causes the material extending distally from the marker 32 to be melted and to flow proximally over the marker 32 in a manner covering the outer surface thereof and encapsulating the same. A portion of this melted material is also formed into the tapered distal end 22 of the sheath 20. The melted material is prevented from flowing into the lumen 28 of the sheath 20 by a mandrel positioned therewithin prior to the initiation of the RF heating process. Advantageously, once the distal portion of the sheath 20 is cooled and removed from within the fixture, the marker 32 is completely embedded within (i.e., encapsulated by) the sheath 20 in the manner shown in FIG. 8. It will be recognized by those of ordinary skill in the art that alternative methods may be employed to facilitate the encapsulation of the marker 32 within the sheath 20 other than for the previously described RF heating process.

As previously indicated, the proximal end 24 of the sheath 20 is itself coupled to the valve head 26 of the sheath assembly 16. In the preferred embodiment, the proximal portion of the sheath 20 includes a tubular reinforcement sleeve 38 disposed thereon to prevent the sheath 20 from buckling relative to the valve head 26 when the same is coupled thereto. The sleeve 38 is typically secured to the outer surface of the proximal portion of the sheath 20 either through the use of adhesives or a shrink fitting technique. Additionally, the sleeve 38 is preferably fabricated from the same material as the sheath 20, i.e., polypropylene.

Referring now to FIGS. 2b and 2c, the valve head 26 of the sheath assembly 16 comprises a hollow, tubular housing 40 including open proximal and distal ends 42, 44. The distal end 44 is defined by a reduced diameter, externally threaded distal portion 46 of the housing 40. Partially inserted into and attached to the proximal end 42 of the housing 40 is a tubular sleeve 48 which itself includes a reduced diameter, externally threaded proximal portion 50. Formed on the outer surface of the housing 40 and extending angularly therefrom is a tubular side arm 52 defining a passage 54 which fluidly communicates with the interior of the housing 40.

Referring now to FIGS. 2b, 2c, 5a and 5b, disposed within the interior of the housing 40 and abutted against the distal end of the sleeve 48 is a second sealing valve or cross slit valve 56. The cross slit valve 56 has a generally cylindrical configuration, and includes an annular proximal portion 58 which defines a beveled inner surface 60. In addition to the proximal portion 58, the cross slit valve 56 includes a generally semi-spherical central portion 62 which defines a concave, semi-spherical proximal surface 64. In this respect, the beveled inner surface of the proximal portion 58 transitions into the semi-spherical proximal surface 64 of the central portion 62. Extending through the apex of the central portion 62 is an aperture 66.

The cross slit valve 56 further includes an annular distal portion 68 which extends distally from the central portion 62 thereof. Extending radially between the inner surface of the distal portion 68 and the convex, semi-spherical distal surface of the central portion 62 are four (4) reinforcement ribs 70. The reinforcement ribs 70 are preferably positioned in equidistantly spaced relation to each other, i.e., in intervals of approximately 90 degrees.

Figure 5A:
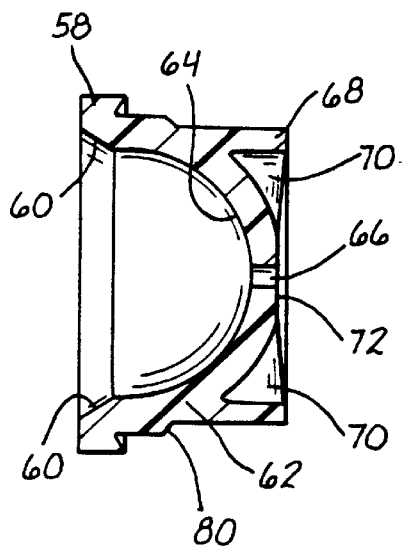
FIG. 5a is a cross-sectional view of the cross slit valve included in the valve head shown in FIGS. 2b and 2c.
Figure 5B:
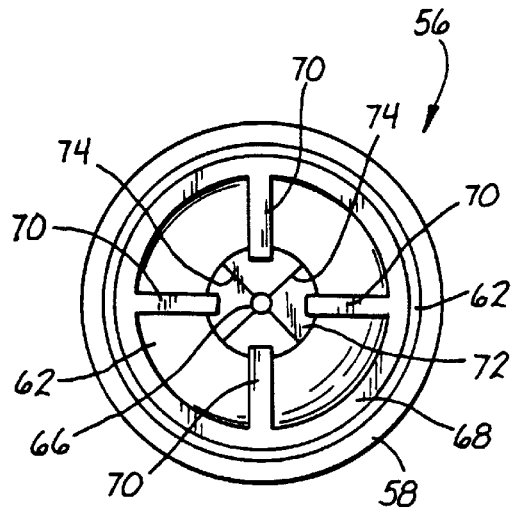

As best seen in FIGS. 5a and 5b, the aperture 66 extending through the central portion 62 is circumvented by a circularly configured region 72 of the distal surface of the central portion 62 which has a generally planar or flat configuration. In addition to the aperture, disposed within the central portion 62 of the cross slit valve 56 is a pair of slits 74 which extend diametrically across the region 72 in perpendicular relation to each other. In this respect, the slits 74 bisect each other at the axis of the aperture 66, and therefore form four (4) identically sized flap portions within the central portion 62. The slits 74, and hence the flap portions, are confined within (i.e., do not extend beyond) the circularly configured region 72 of the central portion 62. As best seen in FIG. 5, the slits 74 preferably do not extend linearly between respective ones of the opposed pairs of ribs 70, but rather are offset from the ribs 70 by approximately 45 degrees, as shown.

In the preferred embodiment, the cross slit valve 56 is fabricated from polyisoprene, though similar biocompatible resilient materials may be used as an alternative. Additionally, the preferred diameter of the aperture 66 is approximately 0.033 inches, with the preferred diameter of the circular region 72 being approximately 0.200 inches. The importance of these particular sizings of the aperture 66 and distal surface region 72 will be discussed in more detail below.

As seen in FIGS. 2b and 2c, the cross slit valve 56 is disposed within the interior of the housing 40 such that the proximal portion 58 is abutted against the distal end of the sleeve 48 of the valve head 26. More particularly, the beveled inner surface 60 of the proximal portion 58 is firmly seated against the complementary, beveled outer surface of an annular, inclined flange portion 76 of the sleeve 48 which defines the distal end thereof. In this respect, the engagement between the inner surface 60 of the proximal portion 58 and the outer surface of the flange portion 76 facilitates the formation of a fluid-tight seal between the sleeve 48 and cross slit valve 56.

In the preferred embodiment, the central and distal portions 62, 68 of the cross slit valve 56 are inserted into a tubular spacer member 78 prior to the placement of the cross slit valve 56 into the hollow interior of the housing 40. As best seen in FIG. 2b, the inner surface of the spacer member 78 is not uniform, but rather has a stepped configuration so as to accommodate the continuous, annular shoulder 80 defined between the outer surfaces of the central and distal portions 62, 68 of the cross slit valve 56. In this respect, when the cross slit valve 56 is fully inserted into the spacer member 78, the proximal portion 58 is abutted against the proximal end of the spacer member 78, with the distal end of the cross slit valve 56 being substantially flush with the distal end of the spacer member 78. As such, when the cross slit valve 56 is placed into sealed engagement with the sleeve 48 in the aforementioned manner, the peripheral edge of the proximal portion 58 and the outer surface of the spacer member 78 are in direct contact with the inner surface of the housing 40.

Figure 4B:
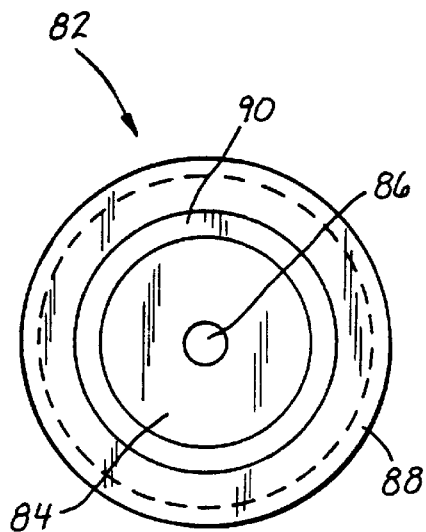

In addition to the cross slit valve 56, also disposed within the hollow interior of the housing 40 of the valve head 26 is a circularly configured first sealing valve or disc valve 82. As best seen in FIGS. 4a and 4b, the disc valve 82 includes a circularly configured main body portion 84 having an aperture 86 disposed within and extending through the center thereof. Formed about the periphery of the proximal surface of the main body portion 84 and extending therefrom is a continuous rim portion 88, while extending from the distal surface of the main body portion 84 is an annular flange portion 90, the diameter of which is less than that of the rim portion 88. The rim portion 88 itself defines a beveled inner surface 91 which slopes at an angle of approximately 45 degrees relative to the proximal surface of the main body portion 84.

Like the cross slit valve 56, the disc valve 82 is also preferably fabricated from polyisoprene, with the aperture 86 having a preferred diameter of approximately 0.075 inches, and the flange portion 90 having a preferred inner diameter of approximately 0.366 inches. In the valve head 26, the disc valve 82 is positioned within the interior of the housing 40 such that the rim portion 88 thereof is firmly engaged to and sealed against the distal end of the spacer member 78, with the proximal surface of the main body portion 84 being in direct contact with the distal end of the cross slit valve 56 (i.e., the distal portion 68 and ribs 70). When the disc valve 82 is oriented in the aforementioned manner, the aperture 86 thereof is coaxially aligned with the aperture 66 of the cross slit valve 56.

The valve head 26 of the sheath assembly 16 further includes a hemostatic valve 92 which is also disposed within the hollow interior of the housing 40 and is preferably a duck bill style valve. As best seen in FIGS. 3a and 3b, the hemostatic valve 92 is configured similarly to the cross slit valve 54, and includes an annular proximal portion 94 which defines the proximal end of the hemostatic valve 92. The proximal portion 94 transitions into a reduced diameter central portion 96 which defines an opposed pair of identically configured flaps 98. Extending distally from the central portion 96 is a tubular, cylindrically configured distal portion 100, the outer diameter of which is slightly less than that of the central portion 96. Integrally connected to and extending perpendicularly between the outer surfaces of the flaps 98 and the inner surface of the distal portion 100 is an opposed pair of linearly aligned ribs 102. Additionally, extending between the distal ends of the flaps 98 is an elongate slit 104 which is oriented in generally perpendicular relation to one of the ribs 102.

As in the previously described cross slit valve 56 and 35 disc valve 82, the hemostatic valve 92 is preferably fabricated from polyisoprene. The hemostatic valve 92 is positioned within the interior of the housing 40 such that the proximal portion 94 thereof is firmly seated against the distal surface of the main body portion 84 of the disc valve 82. When the proximal end of the hemostatic valve 92 defined by the proximal portion 94 is abutted against the distal surface of the main body portion 84, the outer surface of the flange portion 90 of the disc valve 82 extends about the inner surface of the proximal portion 94 of the hemostatic valve 92 in direct contact therewith. The engagement between the flange portion 90 of the disc valve 82 and the proximal portion 94 of the hemostatic valve 92 creates a fluid-tight seal therebetween. When the hemostatic valve 92 is seated against the disc valve 82 in the aforementioned manner, the outer surfaces of the proximal, central and distal portions 94, 96, 100 of the hemostatic valve 92 are in direct contact with the inner surface of the housing 40. In this respect, as best seen in FIG. 2b, the inner surface of the housing 40 is not uniform, but rather has a stepped configuration which is complementary to and accommodates the continuous, stepped annular shoulders defined between the proximal, central and distal portions 94, 96, 100 of the hemostatic valve 92.

In the preferred embodiment, when the valve head 26 of the sheath assembly 16 is assembled in the manner shown in FIG. 2b, the slit 104 is bisected by the coaxially aligned axes of the apertures 66, 86 of the cross slit and disc valves 56, 82. Additionally, the cross slit, disc and hemostatic valves 56, 82, 92 are positioned within the interior of the housing 40 between the sleeve 48 and side arm 52, with the cross slit valve 56 being disposed closest to the proximal end 42 of the housing 40, the hemostatic valve 92 being disposed closest to the distal end 44 of the housing 40, and the disc valve 82 being disposed between the cross slit and hemostatic valves 56, 92. As further seen in FIG. 2b, the proximal portions 58, 94 of the cross slit and hemostatic valves 56, 92 and the peripheral portion of the disc valve 82 are compressed and rigidly captured between the sleeve 48 and a pair of continuous shoulders defined within the inner surface of the housing 40, thus preventing any movement or shifting of the cross slit, disc and hemostatic valves 56, 82, 92 therewithin.

In the sheath assembly 16, the proximal end 24 of the sheath 20 is attached to the distal portion 46 of the housing 40 such that the lumen 28 of the sheath 20 communicates with the interior of the housing 40. In the preferred embodiment, the sheath 20 is selectively detachable from the valve head 26, and in particular the housing 40 thereof, thus allowing the sheath 20 to be replaced with an alternative sheath having a different configuration or fabricated from a different material. The side arm 52 of the housing 40 may be used to facilitate the placement of a tubular fluid line 106 inserted thereinto into fluid communication with the interior of the housing 40, and hence the lumen 28 of the sheath 20. In the sheath assembly 16, each of the valves 56, 82, 92 disposed within the valve head 26 serves a particular function when the introducer assembly 14 is used to facilitate the advancement of the catheter assembly 10 to a desired anatomical site. The precise functionality of the cross slit, disc and hemostatic valves 56, 82, 92 will be described in more detail below.

1. Dilator

In addition to the sheath assembly 16, the introducer assembly 14 of the present invention includes the elongate, tubular dilator 18 shown in FIG. 1c. The dilator 18 includes a tapered distal end 108, a proximal end 110 and a guidewire lumen 112 extending longitudinally (i.e., axially) therethrough which is defined by a luminal surface 114. As best seen in FIG. 2a, the dilator 18 is preferably fabricated from co-extruded tubing which includes an inner layer 116 having the lumen 112 extending axially therethrough, and an integral outer layer 118. The outer layer 118 is preferably fabricated from a mixture of 90% high density polyethylene (e.g., Dow HDPE Resin 08054N, Dow Chemical Co., Midland, Mich.) and 10% low density polyethylene (e.g., Dow LDPE Resin 722M, Dow Chemical Co., Midland, Mich.) The inner layer 116 preferably is fabricated from an Ethylene Vinyl Acetate copolymer (e.g., EVA copolymer LD 306.58, Exxon Chemical Company, Polymers Group). Both the inner and outer layers 116, 118 include a barium sulfate component (approximately 10%) to make the same radiopaque. The preferred diameter of the dilator 18 (i.e., the outer layer 118) is approximately 0.233 inches. Those of ordinary skill in the art will recognize that materials possessing similar characteristics to those previously described may alternatively be used to fabricate the inner and outer layers 116, 118.

As shown in FIGS. 1c and 2a, the distal portion of the dilator 18 which defines the distal end 108 thereof has a tapered configuration. The tapered distal portion of the dilator 18 is preferably formed by initially removing a section of the outer layer 118 from the distal portion of the inner layer 116. Such removal is typically facilitated through the use of a grinding process, with a section of the outer layer 118 having a preferred length of approximately 3.0 inches and extending to the distal end 108 being removed from the inner layer 116. Subsequent to the removal of the outer layer 118 from the inner layer 116, the exposed distal portion of the inner layer 116 (which is approximately 3.0 inches in length) is inserted into a suitable fixture and subjected to an RF heating process which causes the same to assume a tapered configuration.

As further seen in FIG. 2a, the initiation of the RF heating process causes the diameter of the lumen 112 extending through the tapered distal portion of the dilator 18 to be reduced to approximately ½ the diameter of the remainder thereof. As such, the luminal surface 114 of the dilator 18 is not uniform throughout its entire length, but rather defines a beveled shoulder 115 where it transitions into the reduced diameter section of the lumen 112. The preferred diameter of the reduced section of the lumen 112 is approximately 0.037 inches, with the preferred diameter of the remainder of the lumen 112 being approximately 0.070 inches. The distal portion of the lumen 112 is prevented from completely collapsing during the RF heating process by the insertion of a mandrel into the distal portion of the dilator 18 prior to the insertion thereof into the forming fixture. It will be recognized that alternative methods may be employed to facilitate the formation of the distal portion of the dilator 18 with the tapered configuration.

The relatively soft, tapered distal portion of the dilator 18 consisting of the protruding portion of the inner layer 116 is sufficiently soft to be advanced through tortuous blood vessels or other anatomical structures without causing undue trauma or perforation thereof. The proximal portion of the dilator 18 having the outer layer 118 disposed thereon is stiff enough to cause relatively pliable anatomical structures (e.g., blood vessels) to conform to the configuration thereof. In this manner, when the dilator 18 is positioned within a surrounding introducer sheath and is advanced through blood vessels, such as the femoral and iliac blood vessels, the relatively stiff proximal portion of the dilator will cause such blood vessels to assume a more linear or less tortuous configuration, thereby facilitating desired advancement of the introducer sheath to its intended location (e.g., in the abdominal aorta).

3. Assembly of the Introducer Assembly

Referring now to FIG. 2, the introducer assembly 14 of the endovascular delivery system of the present invention is assembled by advancing the dilator 18 through the sheath assembly 16 such that the tapered distal portion of the dilator 18 protrudes from the distal end 22 of the sheath 20. In this respect, the dilator 18 is preferably oriented such that the tapered distal portion of the sheath 20 makes a smooth transition to the tapered distal portion of the dilator 18.

As will be recognized, when positioned within the sheath assembly 16 in the aforementioned manner, the dilator 18 extends through the valve head 26, and more particularly the cross slit, disc and hemostatic valves 56, 82, 92 disposed therewithin. When extended through the cross slit valve 56, the dilator 18 displaces the flap portions defined by the cross slit valve 56 distally within the interior of the housing 40. Though the maximum width of the opening defined by the displaced flap portions is only approximately 0.200 inches (the length of the slits 74), the resiliency of the material used to fabricate the cross slit valve 56 allows the larger diameter dilator 18 (at 0.233 inches) to be advanced through the opening. Similarly, the resiliency of the material used to fabricate the disc valve 82 allows the dilator 18 to be advanced through the aperture 86 (having a diameter of 0.075 inches) thereof. The resiliency of the hemostatic valve 92 allows the flaps 98 thereof to be forced outwardly away from each other when the dilator 18 is advanced through the slit 104 therebetween. Though the ribs 102 extending between the flaps 98 and the distal portion 100 of the hemostatic valve 92 aid in biasing the flaps 98, and more particularly the slit 104, to a normally closed position, the ribs 102 are easily collapsed by the extension of the dilator 18 through the flaps 98 of the hemostatic valve 92.

As will be recognized, due to the diameter of the dilator 18 exceeding the maximum width of the opening defined by the cross slit valve 56 and the diameter of the aperture 86 of the disc valve 82, both the cross slit and disc valves 56, 82 form fluid-tight seals against the dilator 18 when the same is extended through the valve head 26 of the sheath assembly 16. A fluid-tight seal is not created between the hemostatic valve 92 and dilator 18 since the flaps 98 do not close completely about the dilator 18.

4. Preferred Method of Using the Introducer Assembly

The introducer assembly 14 of the endovascular delivery system of the present invention is typically utilized by advancing the same over and along an in situ guidewire. The preferred diameter of the guidewire with which the introducer assembly 14 is utilized is approximately 0.037 inches. As will be recognized, the guidewire passes through the lumen 112 of the dilator 18 when the introducer assembly 14 is advanced thereover.

Once the introducer assembly 14, and more particularly the distal end 108 of the dilator 18, has assumed a desired intraluminal position, the dilator 18 is proximally retracted along the guidewire and completely removed from within the sheath assembly 16. Once the dilator 18 has been withdrawn from within the sheath assembly 16, only the guidewire extends therethrough. Since the diameter of the guidewire (i.e., 0.037 inches) exceeds the diameter of the aperture 66 of the cross slit valve 56 (i.e., 0.033 inches), the cross slit valve 56 forms a fluid-tight seal about the guidewire. As such, blood entering the sheath 20 of the sheath assembly 16 via the open distal end 22 thereof is prevented from flowing proximally through the valve head 26 and out the open proximal end of the sleeve 48 of the valve head 26.

A more detailed discussion regarding the preferred manner of using the introducer assembly 14 of the present delivery system for the treatment of an aortic aneurysm is set forth below.

B. Catheter Assembly

The previously described introducer assembly 14 is used to facilitate the operative placement of the catheter assembly 10 (shown in FIG. 1a), and more particularly the graft 12 positioned thereupon, in a desired intraluminal site. The precise structure of the catheter assembly 10 will now be described with particular reference to FIGS. 1a, 6–7, 9 and 9a.

1. Pusher Body

Referring now to FIGS. 1a, 6 and 9, the catheter assembly 10 of the present invention comprises an elongate, tubular pusher body 120 which includes a distal end 122, a proximal end 124, and a lumen 126 extending longitudinally (i.e., axially) therethrough. As best seen in FIG. 6, the distal end 122 of the pusher body 120 is defined by a slightly expanded or flared distal section 128 thereof. In this respect, the outer diameter of the distal section 128 slightly exceeds that of the remainder of the pusher body 120, with the diameter of the segment of the lumen 126 extending through the distal section 128 being slightly greater than the diameter of the remainder of the lumen 126 extending proximally therefrom. The pusher body 120 is preferably fabricated from 90% polypropylene (e.g., Pro-Fax PM Polypropylene Grade 6532 available from Himont Corporation and having a density of approximately 0.902 g/cm$^3$ (ASTMD 792), a tensile strength at yield of 5,050 psi (ASTMD 638) tinsel elongation at yield of 12% (ASTMD 638), flexural modulus (1% secant) of 240 psi×10$^{-3}$ (ASTMD 790b) rockwell hardness (R scale) 91 (ASTMD 785a and notched izod impact strength at 23° C. of 0.8 ft-lbs/in (ASTMD 2.56a) combined with pharmaceutical grade barium sulfate Product No. 1040 from J.T. Baker & Co., though other materials possessing similar characteristics may also be used in the catheter assembly 10.

2. Dual Tube Catheter

Referring now to FIGS. 1a, 6, 6a and 9, the catheter assembly 10 of the present invention further includes an elongate catheter 130 which preferably has a dual tube construction. In this respect, the catheter 130 preferably comprises an elongate outer tube 132 which defines a distal end 134, a proximal end 136, and a hollow lumen 138 extending longitudinally (i.e., axially) therethrough. As best seen in FIG. 6a, attached to the outer surface of the outer tube 132 in relative close proximity to the distal end 134 thereof is an annular, radiopaque marker 140. In the preferred embodiment, the outer tube 132 is fabricated from stainless steel braided nylon (e.g., commercially available as Autochem Besno nylon 11 resin, available from New England Eurathane, Inc., 105 Sackett Point Road, North Haven, Conn. 06473 braided with 0.001×0.005 stainless steel wire No. 304v, available from Ft. Wayne Metals Research Products, Corp., 960 Indianapolis Road, P.O. 9040, Ft. Wayne, Ind. 46899).

In addition to the outer tube 132, the catheter 130 comprises an elongate inner tube 142 which is smaller in diameter than the outer tube 132 and extends through the lumen 138 thereof. The inner tube 142 defines a distal end 144, a proximal end 146, and a hollow lumen 148 extending longitudinally (i.e., axially) therethrough. The inner tube 142 is preferably fabricated from stainless steel braided nylon tubing, which may be the same as that described hereabove as a material of which the outer tube 132 may be formed. The inner tube 142 is slidably extensible distally and retractable proximally relative to the outer tube 132, for reasons which will be discussed in more detail below.

As best seen in FIG. 6a, disposed upon and attached to the inner tube 142 in relative close proximity to the distal end 144 thereof, is tubular sleeve 150. Also disposed upon and attached to the inner tube 142 is a cylindrically configured stop member 152, the proximal end of which is abutted against the distal end of the sleeve 150. Attached to the outer surface of the sleeve 150 approximately midway between the opposed ends thereof is an annular, radiopaque marker 154 which is identically configured to the marker 140. Both the sleeve 150 and stop member 152 are preferably fabricated from the same material as the inner tube 142.

3. Catheter Balloon

Referring now to FIGS. 6–6c and 7, the catheter assembly 10 further comprises an elongate, inflatable catheter balloon 156. As best seen in FIG. 6a, the balloon 156 includes a distal end 158 which is attached to the sleeve 150 and in direct contact with the proximal end of the stop member 152. As such, the marker 154 attached to the sleeve 150 resides within the interior of the balloon 156. In addition to the distal end 158, the balloon 156 defines a proximal end 160 which is attached to the outer tube 132 of the catheter 130 at a point located slightly proximally relative to the marker 140. As such, the marker 140, like the marker 154, resides within the interior of the balloon 156. The markers 140, 154 are disposed in relative close proximity to the proximal and distal ends 160, 158 of the balloon 156, respectively. Since the proximal end 160 of the balloon 156 is attached to the outer tube 132, and the distal end 158 of the balloon 156 is attached to the sleeve 150, and hence the inner tube 142, the extension of the inner tube 142 distally relative to the outer tube 132 facilitates the longitudinal stretching of the balloon 156, the advantages of which will be discussed in more detail below.

In the catheter assembly 10, the inner tube 142 of the catheter 130 is initially oriented in a first, retracted position relative to the outer tube 132. The inner tube 142 is depicted in its retracted position in FIGS. 6, 6a and 6a. The balloon 156 is inflated only when the inner tube 142 is in its retracted orientation.

Referring now to FIGS. 6a and 7, the balloon 156 of the catheter assembly 10, when fully inflated, has a generally uniform, cylindrical configuration. More particularly, the balloon 156, when inflated, defines an elongate main body portion 162 which has a generally circular cross-sectional configuration. Advantageously, the transition between the main body portion 162 and the distal and proximal ends 158, 160 is not defined by elongate, gradually sloping surfaces, but rather is defined by an opposed pair of end walls 164 which, as best seen in FIG. 7, slope at an angle A relative to the sidewall of the balloon 156 defining the main body portion 162 thereof. The angle A preferably does not exceed 10 degrees, and most preferably does not exceed 5 degrees.

When the balloon 156 is fully inflated, the end walls 164 thereof will assume either a generally flat configuration as shown in FIG. 7 or a curvilinear configuration. If each end wall 164 is flat, the leader line extending therefrom (as shown in FIG. 7) for identifying the angle A extends in a co-planar relation to the end wall 164. If the end wall 164 is curvelinear rather than flat, the leader line extends as a tangent or mean line in relation to the end wall 164. It will be recognized that the other leader line for identifying the angle A extends in perpendicular relation to the longitudinal axis of the catheter 130.

In the preferred embodiment, the maximum diameter of the balloon 156, and in particular the main body portion 162 thereof, when fully inflated is in the range of 21 to 25 millimeters, and is preferably about 23 millimeters. Additionally, the length of the main body portion 162 of the balloon 156 is preferably in the range of 60 to 92 millimeters. The balloon 156 is also preferably fabricated from polyester which has a wall thickness of approximately 0.001 inches and is adapted to withstand an inflation pressure of approximately 2 ATM.

During use of the catheter assembly 10, subsequent to the deflation of the balloon 156, the inner tube 142 is moved from its first, retracted position (shown in FIG. 6a) to a second, extended position (shown in FIG. 6c). The distal advancement of the inner tube 142 relative to the outer tube 132 when the inner tube 142 moves from its retracted position to its extended position facilitates the longitudinal stretching of the balloon 156. As will be appreciated, the balloon 156, when de-pressurized, does not return to its initial un-inflated orientation as shown in FIGS. 6 and 6a. Rather, the diameter of the main body portion 162 of the de-pressurized balloon 156 is not significantly different than when the same is pressurized. Thus, to facilitate the collapse of the balloon 156 and hence a substantial reduction in the diameter of the main body portion 162 thereof, the balloon 156 is longitudinally stretched by advancing the inner tube 142 to its extended position shown in FIG. 6c. The advantages attendant to collapsing the balloon 156 in the aforementioned manner will be discussed in more detail below as well.

4. Intraluminal Graft

Referring now to FIGS. 1a and 6, as previously indicated, the catheter assembly 10 of the present endovascular delivery system includes the intraluminal graft 12 initially positioned thereupon. More particularly, the graft 12 is initially disposed upon the balloon 156 of the catheter assembly 10. As best seen in FIG. 6, the overall length of the graft 12 is substantially less than that of the deflated balloon 156, with the distal and proximal ends 158, 160 of the balloon 156 protruding substantially from respective ones of the opposed ends of the graft 12. The graft 12 is preferably centrally positioned between the distal and proximal ends 158, 160 of the balloon 156 for reasons which will be described below.

The graft 12 of the catheter assembly 10 is shown in its initial, collapsed position in FIG. 6. When collapsed, the graft 12 is tightly constricted about the balloon 156, with the overall diameter of the collapsed graft 12 being roughly equal to the diameter of the stop member 152. As further seen in FIG. 6, when the graft 12 is in its initial, collapsed orientation and tightly constricted about the balloon 156, both the proximal end 160 of the balloon 156 and the proximal end of the graft 12 are received into the flared distal section 128 of the pusher body 120. As will be discussed in more detail below, the partial receipt of the graft 12 into the pusher body 120 maintains the graft 12 in its desired orientation intermediate the distal and proximal ends 158, 160 of the balloon 156 as the catheter assembly 10 is slidably advanced through the introducer assembly 14.

As will also be discussed in more detail below, once the graft 12 has assumed a position in a desired intraluminal site, the pusher body 120 of the catheter assembly 10 is proximally retracted relative to the catheter 130, thus removing the proximal end of the graft 12 and the proximal end 160 of the balloon 156 from within the distal section 128 of the pusher body 120. Once the pusher body 120 has been withdrawn from the graft 12 and balloon 156, the subsequent inflation of the balloon 156 in the manner shown in FIGS. 6a and 7 facilitates the concurrent radial expansion of the graft 12 to a second, expanded orientation. After the graft 12 has been fully radially expanded, the balloon 156 is de-pressurized, and subsequently withdrawn from within the graft 12 by the proximal movement of the catheter 130. However, prior to withdrawing the balloon 156 from within the expanded graft 12, the balloon 156 is stretched in the previously described manner so as to prevent the same from inadvertently catching on or interfering with the graft 12 during the withdrawal of the balloon 156 from therewithin.

A more detailed discussion of how the stretching of the balloon 156 prevents the inadvertent interference thereof with the graft 12 is set forth below as well.

5. Loader

Referring now to FIGS. 1a, 6 and 10c, the catheter assembly 10 of the present invention further comprises a rigid loader 166 which is used to facilitate the operative coupling of the catheter assembly 10 to the introducer assembly 14 during use of the present endovascular delivery system. The loader 166 comprises an elongate tube 168 which is slidably positionable along the length of the pusher body 120 in the manner shown in FIG. 1a. The tube 168 includes a proximal end, and a distal end which is defined by a reduced diameter distal section 170 thereof. Attached to the tube 168 in relative close proximity to the distal section 170 is an-internally threaded connector nut 172. The loader 166, and in particular the distal section 170 thereof, is preferably fabricated from a material which is more rigid than the materials used to fabricate the sheath 20 and pusher body 120.

In the catheter assembly 10, the loader 166 is initially oriented such that both the balloon 156 and collapsed graft 12 constricted thereabout are received into the lumen of the tube 168. As such, when the loader 166 is in its desired initial position, only the inner tube 142 of the catheter 130 protrudes from the distal end thereof. As will be discussed in more detail below, the catheter assembly 10 is cooperatively engaged to the sheath assembly 16 of the introducer assembly 14 by initially inserting the distal section 170 of the loader 166 into the valve head 26 of the sheath assembly 16 subsequent to the removal of the dilator 18 from therewithin. More particularly, the distal section 170 of the loader 166 is extended into the sleeve 48 of the valve head 26, with the connector nut 172 being threadably engaged to the externally threaded proximal portion 50 of the sleeve 48. Subsequent to the connection of the loader 166 to the valve head 26 in the aforementioned manner, the pusher body 120 and catheter 130 are distally advancable therethrough.

The distal section 170 of the tube 168 is sized such that when the loader 166 is attached to the valve head 26 via the connector nut 172, the distal section 170 resides within the bore of the sleeve 48, and does not extend through the cross slit valve 56. As such, no portion of the loader 166 extends through any of the valves 56, 82, 92 of the valve head 26. However, when the pusher body 120 of the catheter assembly 10 is distally advanced through the valve head 26 subsequent to the connection of the loader 166 thereto, the disc valve 82 creates a fluid-tight seal about the pusher body 120 when the same is extended through the aperture 86 thereof. In this respect, though the diameter of the pusher body 120 exceeds the diameter of the aperture 86 (i.e., 0.075 inches), the resiliency of the material used to fabricate the disc valve 82 allows the pusher body 120 to be advanced through the aperture 86, with the disc valve 82 being sealed about the outer surface of the pusher body 120. As will be discussed in more detail below as well, after being extended through the valve head 26, the pusher body 120 is distally advanced through the lumen 28 of the sheath 20 until such time as the collapsed graft 12 and flared distal section 128 of the pusher body 120 protrude from the distal end 22 of the sheath 20.

The inclusion of the loader 166 in the catheter assembly 10 provides the additional advantage of allowing the collapsed graft 12 to be accurately pre-positioned relative to the introducer assembly 14 which ensures accuracy in its use and saves time during the performance of a procedure utilizing the catheter assembly 10. Additionally, the inclusion of the loader 166 in the catheter assembly 10 allows the catheter assembly 10 to be sold or packaged separately from the previously described introducer assembly 14. The loader 166 and corresponding receiving portion of the valve head 26 are preferably formed of material which is more rigid than the introducer sheath 20 and pusher body 120, such that the loader 166 will seat correctly within the interfacing portion of the valve head 26, without flexing or distortion thereof, thus ensuring the proper positioning and registry of the loader 166 and the valve head 26 relative to each other. Furthermore, the ability of the loader 166 to be positively engaged (e.g., locked by threadable engagement of the nut 172 to the valve head 26 of the introducer assembly also facilitates and maintains proper registry and positioning of the loader 166 relative to the introducer assembly 14.

6. Proximal Connector Assembly Referring now to FIGS. 1a, 9 and 9a, the catheter assembly 10 of the present invention further includes a proximal connector assembly 174 which is most clearly depicted in FIG. 9. In the preferred embodiment, the proximal connector assembly 174 includes a distal pusher connector 176. The pusher connector 176 is preferably a Y-connector, and includes a tubular body 178 having a lumen extending longitudinally therethrough. Disposed on respective ones of the opposed proximal and distal ends of the body 178 is a pair of connector nuts 180. Additionally, integrally connected to the body 178 and extending angularly therefrom is a tubular side arm 182 which communicates with the lumen of the body 178.

As best seen in FIG. 9, in the catheter assembly 10, the proximal end 124 of the pusher body 120 is connected to the distal end of the body 178 via the connector nut 180 disposed thereupon. When the pusher body 120 is coupled to the pusher connector 176, the lumen 126 of the pusher body 120 fluidly communicates with the lumen of the body 178. The catheter 130 (including the outer and inner tubes 132, 142) extends through the pusher connector 176, and protrudes from the connector nut 180 disposed on the proximal end of the body 178.

In addition to the pusher connector 176, the proximal connector assembly 174 comprises a central balloon connector 184. The balloon connector 184 comprises a main body 186 having a proximal section 188 and a distal section 190 which is rigidly attached to the proximal section 188. Extending longitudinally through the proximal section 188 is a first bore 192, while extending longitudinally through the distal section 190 is a second bore 194 which communicates with the first bore 192. The first bore 192 of the proximal section 188 has a generally square cross-sectional configuration for reasons which will be discussed in more detail below. Disposed on the distal end of the distal section 190 is a distal connector nut 196, while disposed on the proximal end of the proximal section 188 is a proximal connector nut 198. The balloon connector 184 may further include a tubular side arm 200 (shown in phantom in FIGS. 1a and 9) which fluidly communicates with the second bore 194 of the distal section 190. Formed about and extending radially outward from the outer surface of the distal section 190 is a continuous flange 202 against which the distal connector nut 196 is abutted when fully received onto the externally threaded distal end of the distal section 190.

In the catheter assembly 10, the outer tube 132 of the catheter 130 is received into the distal end of the second bore 194 and rigidly attached to the inner surface of the distal section 190 which defines the second bore 194. As seen in FIG. 9, the outer tube 132 extends to approximately the flange 202 extending radially outward from the distal section 190 of the main body 186. The inner tube 142 of the catheter 130 extends longitudinally through the remainder of the main body 186 of the balloon connector 184, and in particular the first and second bores 192, 194 of the proximal and distal sections 188, 190.

Referring now to FIGS. 9 and 9a, disposed upon and rigidly attached to the proximal portion of the inner tube 142 of the catheter 130 is an elongate, tubular sheath 204 which is preferably fabricated from polycarbonate and includes a distal end 206 and a proximal end 208. The attachment of the sheath 204 to the inner tube 142 is preferably facilitated through the use of an adhesive or a heat bonding process, though alternative attachment methods may also be employed. The sheath 204 is positioned upon the inner tube 142 in a manner wherein the proximal end 208 thereof is substantially flush with the proximal end 146 of the inner tube 142. Positioned upon and rigidly attached to the outer surface of the sheath 204 in relative close proximity to the distal end 206 thereof is a generally cubic anti-rotation member 210. The anti-rotation member is preferably attached to the sheath 204 via an adhesive or a heat bonding process.

As further seen in FIG. 9, both the distal portion of the sheath 204 and the anti-rotation member 210 disposed thereupon normally reside within the first bore 192 of the proximal section 188 of the balloon connector 184. The complementary square cross-sectional configurations of the anti-rotation member 210 and first bore 192 prevent the sheath 204, and hence the inner tube 142 of the catheter 130, from being rotated relative to the balloon connector 184. Though prevented from being rotated within the first bore 192 of the proximal section 188, the anti-rotation member 210 is slidably moveable both distally and proximally within the first bore 192 relative to the balloon connector 184. The remainder of the sheath 204 (i.e., approximately ⅔ of the length thereof) protrudes proximally from the balloon connector 184, and more particularly, from the proximal connector nut 198 disposed upon the proximal end of the proximal section 188 of the main body 186.

In addition to the pusher and balloon connectors 176, 184, the proximal connector assembly 174 of the catheter assembly 10 includes a proximal contrast connector 212. The contrast connector 212 includes a hollow, tubular body 214 having a proximal portion 216 which transitions into a reduced diameter distal portion 218. Disposed on the proximal end of the proximal portion 216 is a cap member 220. The contrast connector 212 may further include a tubular side arm 222 (shown in phantom in FIG. 9) which extends angularly from the proximal portion 216 of the body 214 and fluidly communicates with the hollow interior thereof. As an alternative to such side arm 222, there may be provided a Luer fitting or connector on the proximal end of the proximal connector assembly, in communication with the hollow interior thereof, for injection of radiographic contrast medium.

As further seen in FIG. 9, a proximal portion of the sheath 204 surrounding the inner tube 142 is received into the distal portion 218 of the body 214 and rigidly attached to the inner surface thereof. In this respect, the proximal end 208 of the sheath 204 terminates at the frusto-conical region of the body 214 where the proximal portion 216 transitions into the distal portion 218. The attachment of the sheath 204 to the contrast connector 212 facilitates the rigid attachment of the inner tube 142 to the contrast connector 212 as well due to the same being secured to the sheath 204. As will be recognized, due to the proximal portion of the sheath 204 being rigidly attached to the contrast connector 212, the sheath 204 is prevented from rotating relative to the balloon connector 184 by the receipt of the anti-rotation member 210 on the distal portion of the sheath 204 into the complementary first bore 192 of the main body 186.

Attached to that portion of the sheath 204 which extends between the proximal connector nut 198 of the balloon connector 184 and the distal portion 218 of the contrast connector 212 is a spacer clip 224. The spacer clip 224 includes a generally semi-circular body portion 226 which is adapted to releasably engage the sheath 204. Formed on and extending outwardly from one end of the body portion 226 is a pair of ear portions 228. Additionally, attached to and extending between the body portion 226 and the proximal section 188 of the balloon connector 184 is an elongate tether member 230. As seen in FIG. 9 in phantom, the spacer clip 224 is normally positioned upon the exposed portion of the sheath 204 such that the ear portions 228 are abutted against the distal end of the distal portion 218 of the body 214, with the opposite, distal end of the body portion 226 being abutted against the proximal connector nut 198 of the balloon connector 184. When attached to the sheath 204, the spacer clip 224 prevents any longitudinal movement of the contrast connector 212 relative to the balloon connector 184 for reasons which will be discussed in more detail below. The spacer clip 224 is selectively releasable from the sheath 204 by pulling the same therefrom via the ear portions 228.

Once disengaged from the sheath 204, the detached spacer clip 224 is maintained in connection to the catheter assembly 10 via the tether member 230 extending therefrom.

As previously explained, both the proximal end 160 of the balloon 156 and the proximal end of the graft 12 are received into the flared distal section 128 of the pusher body 120, with the partial receipt of the graft 12 into the pusher body 120 maintaining the graft 12 in its desired orientation intermediate the distal and proximal ends 158, 160 of the balloon 156 as the catheter assembly 10 is slidably advanced through the introducer assembly 14. In this respect, the proximal retraction of the pusher body 120 of the catheter assembly 10 relative to the catheter 130 facilitates the removal of the proximal end of the graft 12 and the proximal end 160 of the balloon 156 from within the flared distal section 128 of the pusher body 120.

In the catheter assembly 10, the proximal movement or retraction of the pusher body 120 relative to the catheter 130 is facilitated by tightly grasping the pusher and balloon connectors 176, 184 of the proximal connector assembly 174, and subsequently pulling the pusher connector 176 proximally toward the balloon connector 184. In this respect, since the pusher body 120 is attached to the pusher connector 176 and the outer tube 132 of the catheter 130 is attached to the balloon connector 184, the pulling of the pusher connector 176 toward the balloon connector 184 facilitates the proximal advancement of the pusher connector 176 along the catheter 130 (and in particular its outer tube 132), thereby resulting in the concurrent proximal retraction of the pusher body 120 relative to the catheter 130. As previously indicated, the proximal movement of the pusher body 120 along the catheter 130 facilitates the removal of the proximal end of the graft 12 and the proximal end 160 of the balloon 156 from within the flared distal section 128 of the pusher body 120.

As also previously explained, subsequent to being de-pressurized, the balloon 156 is preferably stretched longitudinally by the distal advancement of the inner tube 142 of the catheter 130 relative to the outer tube 132 thereof. More particularly, the inner tube 142 is moved from its first, retracted position (shown in FIG. 6b) to its second, extended position (shown in FIG. 6c). The movement of the inner tube 142 from its retracted position to its extended position to stretch the balloon 156 is facilitated by tightly grasping the balloon and contrast connectors 184, 212 of the proximal connector assembly 174, and subsequently pushing the contrast connector 212 distally toward the balloon connector 184. In this respect, since the outer tube 132 is rigidly attached to the balloon connector 184 and the inner tube 142 is rigidly attached to the contrast connector 212 via the sheath 204, the movement of the contrast connector 212 toward the balloon connector 184 results in the slidable advancement of the inner tube 142 distally within the outer tube 132.

As a result, the attachment of the spacer clip 224 to the exposed portion of the sheath 20 in the aforementioned manner prevents the contrast connector 212 from being moved distally toward the balloon connector 184. As such, while the spacer clip 224 is in its operative position upon the sheath 204, the balloon 156 cannot be longitudinally stretched in that the inner tube 142 is prevented from moving from its first, retracted position to its second, extended position. Once the spacer clip 224 is detached from the sheath 204, the balloon and contrast connectors 184, 212 are not longer maintained in spaced relation to each other so that the contrast connector 212 can be pushed distally toward the balloon connector 184, thereby facilitating the distal advancement of the inner tube 142 to its extended position and the resultant stretching of the de-pressurized balloon 156.

C. Preferred Method of Using the Present Endovascular Delivery System

Having thus described the various components comprising the endovascular delivery system of the present invention, an exemplary method of utilizing the same in relation to the treatment of aortic aneurysms will now be described with particular reference to FIGS. 10a–10h.

Referring now to FIG. 10a, the endovascular delivery system of the present invention is used by initially advancing a guidewire 232 into a femoral artery and into a site in the aorta 234 which includes an aortic aneurysm 236. As previously indicated, aortic aneurysms are commonly located between the left and right iliac arteries and the renal arteries. The introduction of the guidewire 232 into the femoral artery is facilitated in a conventional manner, with the guidewire 232 having a preferred diameter of approximately 0.037 inches. The guidewire 232 is fully extended through that region of the aorta 234 including the aortic aneurysm 236.

As further seen in FIG. 10a, subsequent to the extension of the guidewire 232 through the aortic aneurysm 236, the introducer assembly 14 of the present endovascular delivery system is advanced over the guidewire 232. In this respect, the exposed proximal end of the guidewire 232 is inserted into the distal end 108 of the dilator 18, and more particularly the lumen 112 thereof. In the introducer assembly 14, the proximal end 110 of the dilator 18 protrudes proximally from the valve head 26 of the sheath assembly 16, with the advancement of the introducer assembly 14 along the guidewire 232 eventually resulting in the protrusion of the guidewire 232 from the proximal end 110 of the dilator 18. Advantageously, the tapered configuration of the distal portion of the dilator 18 assists in the intraluminal advancement of the introducer assembly 14 to the site of the aortic aneurysm 236.

Referring now to FIGS. 10a and 10b, the introducer assembly 14 is advanced into the aorta 234 to a point wherein the distal end 22 of the sheath 20 is positioned adjacent to (but not within) the aortic aneurysm 236. Due to the above described fluid-tight seals created between the cross slit and disc valves 56, 82 and the dilator 18 when the same is extended through the valve head 26 of the sheath assembly 16, any blood seeping into the introducer assembly 14 between the dilator 18 and the distal end 22 of the sheath 20 is prevented from flowing out of the valve head 26. As will be recognized, when the distal end 22 of the sheath 20 assumes the aforementioned position within the aorta 234, the valve head 26 of the introducer assembly 14 remains externally disposed. Advantageously, the inclusion of the embedded radiopaque marker 32 within the sheath 20 adjacent the distal end 22 thereof allows the distal end 22 to be accurately positioned relative to the aortic aneurysm 236.

Once the distal end 22 of the sheath 20 has been positioned adjacent the aortic aneurysm 236, the dilator 18 is proximally withdrawn from within the introducer assembly 14, with only the sheath 20 of the sheath assembly 16 and the guidewire 232 remaining in situ. As will be recognized, the dilator 18 is proximally advanced along the guidewire 232 as the dilator 18 is being withdrawn from within the sheath assembly 16. Once the dilator 18 is completely removed from within the sheath assembly 16, only the guidewire 232 extends longitudinally therethrough.

Blood entering the distal end 22 of the sheath 20 and flowing through the lumen 28 thereof along the guidewire 232 is prevented from escaping the valve head 26 by the previously described fluid-tight seal created between the cross slit valve 56 and the guidewire 232. In this respect, as previously indicated, the preferred diameter of the guidewire 232 is approximately 0.037 inches, with the preferred diameter of the aperture 66 of the cross slit valve 56 being approximately 0.033 inches, thus facilitating the formation of the fluid-tight seal about the guidewire 232.

Referring now to FIG. 10c, subsequent to the withdrawal of the dilator 18 from within the sheath assembly 16, the catheter assembly 10 is operatively coupled to the sheath assembly 16, and in particular the valve head 26 thereof, via the loader 166. Such cooperative engagement is facilitated by initially inserting the exposed proximal end of the guidewire 232 into the distal end 144 of the inner tube 142 of the catheter 130, and more particularly the lumen 148 thereof. Thereafter, the distal section 170 of the loader 166 is inserted into the sleeve 48 of the valve head 26, with the connector nut 172 being threadably engaged to the externally threaded proximal portion 50 of the sleeve 48. The engagement of the connector nut 172 to the proximal portion 50 of the sleeve 48 facilitates the rigid attachment of the loader 166 to the valve head 26. It is contemplated herein that alternative methods may be employed to facilitate the rigid attachment of the loader 166 to the valve head 26 other than for the use of the internally threaded connector nut 172, (e.g., the use of a bayonet connection).

As previously explained, when the catheter assembly 10 is initially connected to the sheath assembly 16 in the aforementioned manner, both the balloon 156 and the graft 12 collapsed thereabout reside within the tube 168 of the loader 166. In this respect, only a relatively small segment of the inner tube 142 of the catheter 130 protrudes distally from the distal section 170 of the tube 168. When the loader 166 is attached to the valve head 26 via the connector nut 172, the distal section 170 of the tube 168 resides within the bore of the sleeve 48, and does not extend through the cross slit valve 56.

Figure 10E:
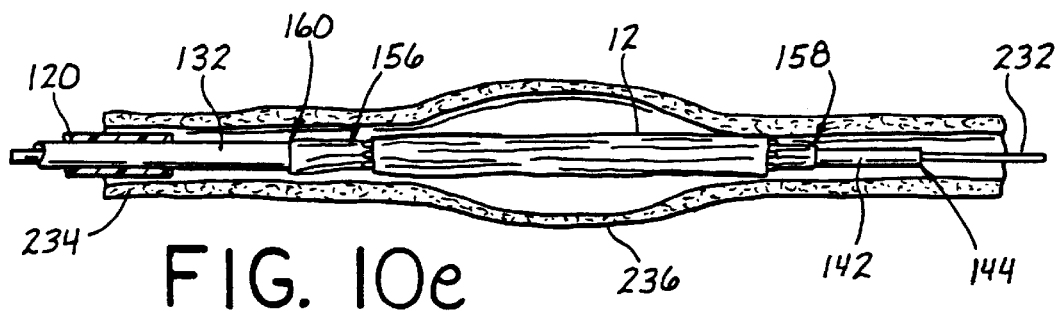

Referring now to FIGS. 10d and 10e, subsequent to the connection of the loader 166 to the valve head 26 in the aforementioned manner, the catheter assembly 10 is slidably advanced along the guidewire 232 through the valve head 26 and lumen 28 of the sheath 20. More specifically, the pusher body 120 and catheter 130 of the catheter assembly 10 are distally advanced through the sheath assembly 16, and in particular the valve head 26 and sheath 20 thereof. The distal advancement of the catheter assembly 10 through the sheath assembly 16 is continued until such time as the flared distal section 128 of the pusher body 120 protrudes from the distal end 22 of the sheath 20.

As previously explained, when the catheter assembly 10 is initially advanced through the sheath assembly 16, both the proximal end 160 of the balloon 156 and the proximal end of the graft 12 reside within the flared distal section 128 of the pusher body 120, and are compressed between the inner surface of the distal section 128 and the outer surface of the outer tube 132 of the catheter 130. When the pusher body 120 is distally advanced through the sheath assembly 16 subsequent to the connection of the loader 166 thereto, the disc valve 82 creates a fluid-tight seal about the pusher body 120 in the above described manner. Thus, any blood seeping into the sheath 20 between the distal end 22 thereof and the outer surface of the pusher body 120 is prevented from escaping the valve head 26 of the sheath assembly 16.

As further seen in FIG. 10e, the pusher body 120 is distally advanced from the sheath 20 such that graft 12 collapsed about the balloon 156 is centrally positioned within the aortic aneurysm 236. The graft 12 is sized such that the proximal and distal ends thereof protrude beyond the opposed boundaries of the aortic aneurysm 236 and into unaffected regions of the aorta 234. Since the graft 12 is centrally positioned upon the balloon 156, the radiopaque markers 140, 154 disposed adjacent respective ones of the distal and proximal ends 158, 160 of the balloon 156 (which protrude from respective ones of the opposed ends of the graft 12) assist in the precise positioning of the graft 12 relative to the aortic aneurysm 236.

Once the graft 12 has been properly positioned relative to the aortic aneurysm 236, the flared distal section 128 of the pusher body 120 is proximally retracted from about the proximal end of the graft 12 and the proximal end 160 of the balloon 156. As previously explained, such proximal retraction of the pusher body 120 relative to the catheter 130 is facilitated by tightly grasping the pusher and balloon connectors 176, 184 of the proximal connector assembly 174, and subsequently pulling the pusher connector 176 proximally toward the balloon connector 184. In this respect, the pulling of the pusher connector 176 toward the balloon connector 184 facilitates the proximal movement of the pusher connector 176 along the catheter 130 (and in particular its outer tube 132), thereby resulting in the concurrent proximal retraction of the pusher body 120 relative to the catheter 130. Such proximal movement facilitates the removal of the proximal end of the graft 12 and the proximal end 160 of the balloon 156 from within the flared distal section 128 of the pusher body 120. It is contemplated herein that the catheter assembly 10 may be configured in a manner wherein the retraction of the pusher body 120 from about the proximal end of the graft 12 and the proximal end 150 of the balloon 156 occurs as an automatic event, (e.g., is functionally linked to the inflation of the balloon 156).

Figure 10F:
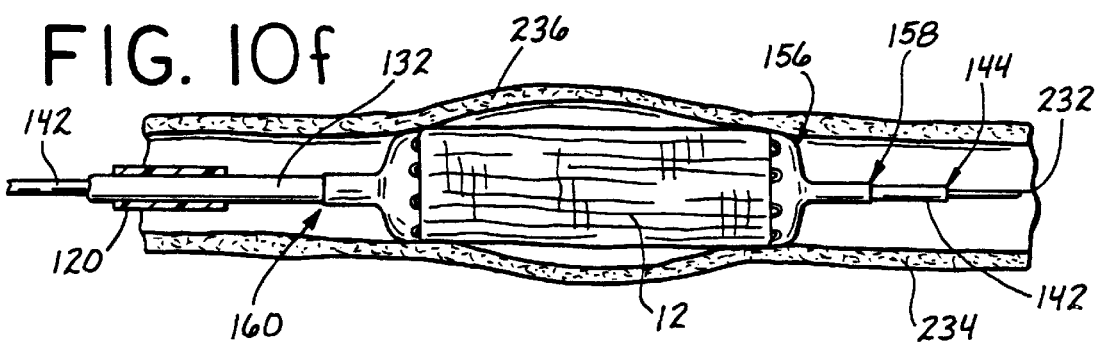

Referring now to FIG. 10f, after the pusher body 120 has been proximally retracted relative to the catheter 130, and more particularly the balloon 156 and graft 12 positioned thereupon, the balloon 156 is inflated via the balloon connector 184 and through lumen 138. As seen in FIG. 10f, the inflation/pressurization of the balloon 156 facilitates the concurrent radial expansion of the graft 12 from its initial, collapsed orientation, to its second, expanded orientation.

When the graft 12 is fully expanded, the opposed ends thereof engage the luminal surfaces of unaffected regions of the aorta 234, with the graft 12 effectively "bridging" the aortic aneurysm 236. Due to the configuration of the balloon 156 when fully inflated, the radial expansion of the graft 12 to its second, expanded orientation is uniform. In this respect, the expansive forces applied to the opposed ends of the graft 12 by the balloon 156 are equal to those applied to the remainder thereof. This uniform application of expansive forces to the graft 12 facilitates the tight engagement of the opposed ends thereof to the luminal surface of the aorta 234.

Figure 10G:
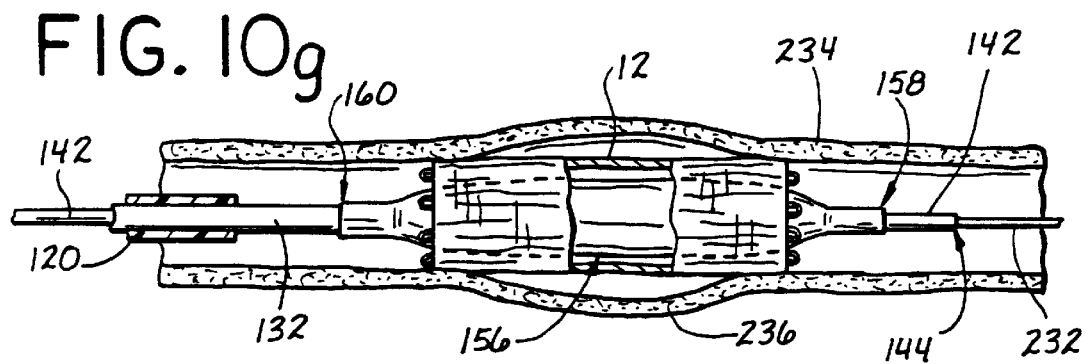

Referring now to FIG. 10g, after the graft 12 has been radially expanded in the aforementioned manner, the balloon 156 is de-pressurized. However, as previously explained, when the balloon 156 is de-pressurized, it may not return to its initial, un-inflated orientation as shown in FIGS. 6 and 6a due to rigidity of the balloon material. Rather, the diameter of the main body portion 162 of the de-pressurized balloon 156 may remain substantially the same as when the balloon 156 is fully inflated, or may otherwise continue to protrude in a manner which could complicate subsequent retraction and removal of the delivery catheter.

Figure 10H:
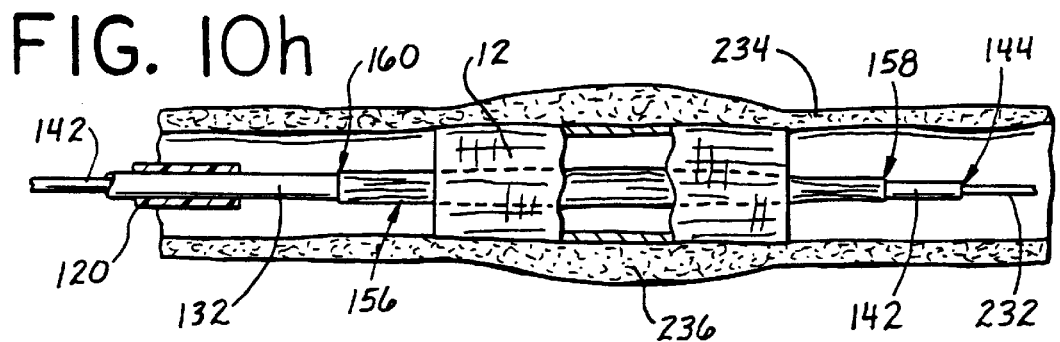

Referring now to FIGS. 10g and 10h, to prevent the de-pressurized balloon 156 from inadvertently catching on or interfering with the radially expanded graft 12 during the withdrawal of the balloon 156 from therewithin, the balloon 156 is longitudinally stretched in the previously described manner prior to the withdrawal of the catheter 130 from within the graft 12. As previously explained, such stretching of the de-pressurized balloon 156 is accomplished by distally advancing the inner tube 142 of the catheter 130 relative to the outer tube 132 thereof. Such movement of the inner tube 142 is facilitated by tightly grasping the balloon and contrast connectors 184, 212 of the proximal connector assembly 174, and subsequently pushing the contrast connector 212 distally toward the balloon connector 184. As also previously explained, the spacer clip 224 must be removed from the exposed portion of the sheath 204 of the proximal connector assembly 174 to allow the contrast connector 212 to be pushed toward the balloon connector 184. It is contemplated that alternative methods may be employed to facilitate the manipulation of the balloon 156 into a faut configuration, (e.g., twisting the balloon 156 rather than longitudinally stretching the balloon 156).

Once longitudinally stretched, the balloon 156 is substantially collapsed in the manner shown in FIG. 10h. Once the balloon 156 is collapsed, the catheter assembly 10 is proximally withdrawn from within the graft 12 along the guidewire 232. In this respect, the catheter assembly 10, and more particularly the pusher body 120, catheter 130 and deflated balloon 156, are retracted into the lumen 28 of the sheath 20 of the sheath assembly 16. As a result, the stretching of the balloon 156 in the aforementioned manner prevents the balloon 156 from interfering with the graft 12 during the proximal retraction of the catheter assembly 10 relative thereto.

Once the catheter assembly 10 has been proximally retracted into the sheath 20, the sheath assembly 16 and catheter assembly 10 are withdrawn from within the patient's body, with only the guidewire 232 remaining therewithin. The final step of the preferred method of using the present endovascular delivery system involves removing the guidewire 232 from within the patient's body.

As previously explained, during the use of the present endovascular delivery system the cross slit and disc valves 56, 82 of the valve head 26 create fluid-tight seals against the dilator 18 when the same is extended through the sheath assembly 16, thereby preventing any blood seeping into the introducer assembly 14 between the dilator 18 and the distal end 22 of the sheath 20 from flowing out of the valve head 26. Since only the guidewire 232 extends longitudinally through the sheath assembly 16 once the dilator 18 has been completely removed from therewithin, blood entering the distal end 22 of the sheath 20 and flowing through the lumen 28 thereof along the guidewire 232 is prevented from escaping the valve head 26 by the fluid-tight seal created between the cross slit valve 56 and guidewire 232. When the pusher body 120 is distally advanced through the sheath assembly 16 subsequent to the connection of the loader 166 thereto, the disc valve 82 creates a fluid-tight seal about the pusher body 120, thus preventing any blood seeping into the sheath 20 between the distal end 22 thereof and the outer surface of the pusher body 120 from escaping the valve head 26 of the sheath assembly 16. In the event the guidewire 232 is withdrawn from within the patient's body prior to the retraction of the sheath assembly 16 from therewithin, the hemostasis valve 92 prevents any blood flowing through the lumen 28 of the sheath 20 from escaping the valve head 26 of the sheath assembly 16.

D. Preferred Method of Checking for "Endoleaks" Following Implantation of an Endovascular Graft When the delivery system of the present invention is utilized to implant an endovascular graft within a blood vessel (e.g., for purposes of bridging an aneurysm), it is often desirable to form one or more tests to make certain that the end(s) of the graft are seated in the desired sealing contact with the surrounding blood vessel wall such that blood does not leak into the space between the outer surface of the graft and inner surface of the blood vessel wall. Such leakage of blood into the space between the outer surface of the graft and the inner surface of the blood vessel wall is herein referred to as an "endoleak".

The catheter assembly 10 of the present invention, when constructed in accordance with the above-described preferred embodiment, is equipped to enable the operator to easily inject a radiographic contrast medium to fluoroscopically or radiographically determine whether any such "endoleak(s)" are present. In this regard, one or more optional side apertures 149 may be formed in the side wall of the inner catheter tube 142, near the distal end 144 thereof. After the graft 12 has been radially expanded and implanted at its desired implantation site, and after the balloon 156 has been returned to its deflated state, the guidewire 232 may be extracted and removed, and a radiographic contrast medium may be injected through the guidewire lumen 148 such that said radiographic contrast medium will flow out of the distal end opening of the guidewire lumen 148 and optional side apertures 149. In this manner, a bolus of radiographic contrast medium may be introduced into the bloodflow immediately upstream of the previously-implanted graft 12, such that the radiographic contrast medium will entirely flow through the lumenal passageway of the graft 12 if no endoleaks are present, but will be seen to seep or flow into the space surrounding the graft 12 (e.g., into the cavity of the aneurysm if the graft has been implanted for the purpose of aneurysm treatment) in the event that one or more endoleak(s) are present.

The advantages provided by the present endovascular delivery system over those known in the prior art are numerous. For example, the delivery catheter of the present invention is capable of being longitudinally telescoped or elongated to draw the deflated balloon material from snagging or interfering with retraction and removal of the catheter after the intraluminal prosthesis has been implanted. Also, the delivery catheter of the present invention may incorporate a non-tapered or minimally-tapered balloon which exerts substantially consistent outward pressure over the entire length of the radially expandable intraluminal prosthesis, thereby allowing the prosthesis to be implanted close to or immediately adjacent a vascular bifurcation (e.g., the iliac bifurcation at the inferior end of the abdominal aorta), without the need for additional space to accommodate a protruding tapered portion of the balloon. Additionally, the delivery catheter of the present invention may incorporate a loader assembly which initially slides over and surrounds the radially compact endoluminal prosthesis, such loader assembly being engagable with the proximal end of a tubular introducer, and preferably connectable or lockable thereto, so as to facilitate ease of insertion and introduction of the distal portion of the catheter (including the radially compact endoluminal prosthesis and the underlying balloon), into the lumen of the introducer. Also, the introducer assembly of the present invention may incorporate an embedded radiopaque marker which is fully encapsulated and surrounded by the material of the introducer sheath, thereby providing a smooth, non-traumatic outer surface of the introducer sheath, while allowing the marker to remain readily and apparently visible by radiographic means. Furthermore, the introducer may be provided with a novel valving assembly, as described hereabove, which prevents backflow or leakage of blood from the introducer, while allowing various elongate members (i.e., delivery catheter, dilator), having differing outer diameters to be inserted therethrough. Moreover, the dilator member of the present invention is of a unique construction whereby the distal portion of the dilator is formed of relatively pliable non-traumatic material while the proximal portion of the dilator is sheathed with relatively stiff less pliable material. Additionally, by the above-described construction of the present invention, one initially inserted introducer assembly may be used for passage and implantation of a plurality of endoluminal prosthesis from a plurality of delivery catheters, thereby facilitating replacement of an ill-fitting graft or implantation of multiple graft segments using grafts of modular design, such as those wherein individual segments of tubular grafts are deployed and expanded in overlapping fashion using what is known as a "trombone" technique.

As previously indicated, though being described for use in the treatment of aneurysms, the present endovascular delivery system also finds utility in relation to the implantation of endoprothstetic devices in blood vessels or other anatomical passageways of the body for the treatment of other medical conditions including stenoses and occlusions. It will be recognized that such endoprosthetic devices may include devices other than for the previously described graft 12.

Additional modifications and improvements of the present invention may also be apparent to those skilled in the art. Thus, the particular combination of parts described and illustrated herein is intended to represent only one embodiment of the present invention, and is not intended to serve as limitations of alternative devices within the spirit and scope of the invention.

What is claimed is:

1. Apparatus for delivering an endoluminal stent or prosthesis into the vasculature of a patient comprising:

an introducer having a distal end adapted for insertion into the vasculature, a lumen of a first diameter, and a proximal end;

a catheter body having a balloon mounted on one end, the endoluminal stent or prosthesis being collapsed around the balloon;

a tubular loader for placement outside the patient having a lumen with a diameter equal to or less than the first diameter and a distal end engageable with the introducer proximal end, the lumen of the loader containing the balloon and endoluminal stent or prosthesis collapsed therearound; and a pusher adapted to fit within the lumen of the loader and engage a proximal end of the endoluminal stent or prosthesis;

wherein the introducer proximal end engages with the loader distal end to prevent relative movement of the introducer and the loader; and wherein the lumen of the loader and the introducer lumen form a continuous lumen upon engagement of the loader and the introducer, the continuous lumen extending from outside the patient to a point of implantation in the vasculature, through which the balloon and endoluminal stent or prosthesis collapsed therearound is pushed by the pusher.

2. The apparatus of claim 1 wherein the pusher includes a pusher body having a proximal end, a distal end, and a hollow lumen extending longitudinally therethrough and adapted to receive the balloon catheter such that the balloon protrudes from the distal end of the pusher body.

* * * * *